US011124557B2

(12) United States Patent
Li et al.

(10) Patent No.: US 11,124,557 B2
(45) Date of Patent: Sep. 21, 2021

(54) HIGH-AFFINITY AND SOLUBLE PDL-1 MOLECULE

(71) Applicant: Guangzhou Institutes of Biomedicine and Health, Chinese Academy of Sciences, Guangdong (CN)

(72) Inventors: Yi Li, Guangdong (CN); Zhaoduan Liang, Guangdong (CN)

(73) Assignee: GUANGZHOU INSTITUTES OF BIOMEDICINE AND HEALTH, CHINESE ACADEMY OF SCIENCES, Guangdong (CN)

( * ) Notice: Subject to any disclaimer, the term of this patent is extended or adjusted under 35 U.S.C. 154(b) by 49 days.

(21) Appl. No.: 15/767,334

(22) PCT Filed: Oct. 9, 2016

(86) PCT No.: PCT/CN2016/101597
§ 371 (c)(1),
(2) Date: Apr. 10, 2018

(87) PCT Pub. No.: WO2017/059819
PCT Pub. Date: Apr. 13, 2017

(65) Prior Publication Data
US 2018/0291081 A1 Oct. 11, 2018

(30) Foreign Application Priority Data
Oct. 10, 2015 (CN) .......................... 201510653647.9

(51) Int. Cl.
*A61K 38/16* (2006.01)
*A61K 38/00* (2006.01)
*A61P 35/00* (2006.01)
*C07K 1/00* (2006.01)
*C07K 14/00* (2006.01)
*C07K 17/00* (2006.01)
*C07K 14/705* (2006.01)
*A61K 38/17* (2006.01)
*C12N 15/63* (2006.01)

(52) U.S. Cl.
CPC ........ *C07K 14/70532* (2013.01); *A61K 38/16* (2013.01); *A61K 38/17* (2013.01); *A61K 38/1774* (2013.01); *A61P 35/00* (2018.01); *C07K 14/705* (2013.01); *C12N 15/63* (2013.01); *C07K 2319/30* (2013.01)

(58) Field of Classification Search
None
See application file for complete search history.

(56) References Cited
U.S. PATENT DOCUMENTS 9,045,545 B1 * 6/2015 Clube .................. C12Q 1/6883
2011/0195068 A1 * 8/2011 Langermann ........ C07K 14/521
424/133.1
2013/0149305 A1 6/2013 Ostrand-Rosenberg

FOREIGN PATENT DOCUMENTS

CN 102918058 A 2/2013
WO WO-2018022945 A1 * 2/2018 ....... C07K 14/70596

OTHER PUBLICATIONS

UniProt Database, Accession No. G1RCP1, 7 pages (2011) (Year: 2011).*
"Lilly Using Immunocore ImmTAC Technology in Cancer Alliance," Genetic Eng. & Biotechn. News, available online at https://www.genengnews.com/topics/drug-discovery/lilly-using-immunocore-immtac-technology-in-cancer-alliance/, 5 pages (2014) (Year: 2014).*
UniProt Accession No. Q9NZQ7, 10 pages (2000) (Year: 2000).*
International Search Report in PCT/CN2016/101597 dated Apr. 13, 2017; 4 pages (Engliah translation).
Dong, H. et al.; "B7-H1 pathway and its role in the evasion of tumor immunity"; *J Mol Med*; vol. 81; 2003; pp. 281-287.
Karim, R. et al.; "Tumor-Expressed B7-H1 and B7-DC in Relation to PD-1+ T-Cell Infiltration and Survival of Patients with Cervical Carcinoma"; *Clinical Cancer Research*; vol. 15, No. 20; Oct. 15, 2009; pp. 6341-6347.
Konishi, J. et al.; "B7-H1 Expression on Non-Small Cell Lung Cancer Cells and Its Relationship with Tumor-Infiltrating Lymphocytes and Their PD-1 Expression"; *Clinical Cancer Research*; vol. 10; Aug. 1, 2004; pp. 5094-5100.
Li, Y. et al.; "Directed evolution of human T-cell receptors with picomolar affinities by phage display"; *Nature Biotechnology*; vol. 23, No. 3; Mar. 2005; pp. 349-354.
Lin, D.Y. et al.; "The PD-1/PD-L1 complex resembles the antigen-binding Fv domains of antibodies and T cell receptors"; *PNAS*; vol. 105, No. 8; Feb. 26, 2008; pp. 3011-3016.
Nomi, T. et al.; "Clinical Significance and Therapeutic Potential of the Programmed Death-1 Ligand/Programmed Death-1 Pathway in Human Pancreatic Cancer"; *Clinical Cancer Research*; vol. 13, No. 7; Apr. 1, 2007; pp. 2151-2157.

(Continued)

*Primary Examiner* — Thea D'Ambrosio
(74) *Attorney, Agent, or Firm* — Kilpatrick Townsend & Stockton LLP

(57) ABSTRACT

Provided in the present invention is a PDL-1 molecule. The affinity of the PDL-1 molecule to the PD-1 molecule is at least two times the affinity of the wild-type PDL-1 molecule to the PD-1 molecule. Meanwhile, the PDL-1 molecule of the present invention can effectively improve the killing efficiency of lymphocytes. In addition, the present invention also provides nucleic acids encoding the PDL-1 molecule of the present invention, and a complex of the PDL-1 molecules of the present invention. The PDL-1 molecule of the present invention may be used alone or in combination with other molecules.

8 Claims, 13 Drawing Sheets

Specification includes a Sequence Listing.

(56) References Cited

OTHER PUBLICATIONS

Oates, J. et al.; "Novel bi-specific agents for targeted cancer therapy"; *OncoImmunology*; vol. 2, Issue 2; Feb. 2013; pp. e22891-1-e22891-3.
Radziewicz, H. et al.; "Liver-Infiltrating Lymphocytes in Chronic Human Hepatitis C Virus Infection Display an Exhausted Phenotype with High Levels of PD-1 and Low Levels of CD127 Expression"; *Journal of Virology*; vol. 81, No. 6; Mar. 2007; pp. 2545-2553.
Rashtchian, A.; "Novel methods for cloning and engineering genes using the polymerase chain reaction"; *Current Opinion in Biotechnology*; vol. 6; 1995; pp. 30-36.
Zhao, Q. et al.; "Interleukin-17-educated monocytes suppress cytotoxic T-cell function through B7-H1 in hepatocellular carcinoma patients"; *Eur. J. Immunol.*; vol. 41; 2011; pp. 2314-2322.

\* cited by examiner

FTVTVPKDLYVVEYGSNMTIECKFPVEKQLDLAALIVYWEMEDKNIIQFVHGEEDL
KVQHSSYRQRARLLKDQLSLGNAALQITDVKLQDAGVYRCMISYGGADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:1)

FIG. 1A

TTTACGGTTACGGTTCCGAAAGACCTGTATGTGGTTGAATACGGCTCTAATATG
ACGATTGAATGCAAATTCCCGGTTGAAAAACAACTGGATCTGGCGGCCCTGATT
GTGTATTGGGAAATGGAAGACAAAAACATCATCCAATTCGTGCATGGCGAAGA
AGATCTGAAAGTTCAGCACAGCTCTTACCGTCAACGCGCACGTCTGCTGAAAGA
CCAGCTGAGCCTGGGCAATGCAGCTCTGCAGATCACGGATGTTAAACTGCAAGA
CGCCGGTGTCTATCGCTGCATGATTTCTTATGGCGGTGCAGACTACAAACGTAT
CACCGTCAAAGTGAACGCTCCGTACAACAAAATTAATCAGCGCATCCTGGTGGT
TGATCCGGTTACGTCCGAACATGAACTGACCTGAAGCGGAAGGCTATCCGAAA
GCCGAAGTCATTTGGACCAGTTCCGATCACCAGGTGCTGTCAGGTAAAACCACG
ACCACGAACTCGAAACGCGAAGAAAACTGTTTAATGTCACGAGCACCCTGCG
TATTAACACCACGACCAATGAAATCTTCTACTGCACCTTTCGTCGTCTGGACCCG
GAAGAAAATCATACGGCGGAACTGGTTATCCCGGAACTG
(SEQ ID NO:2)

FIG.1B

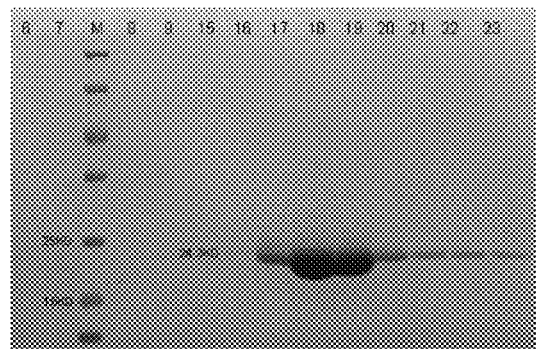

FIG. 2

MANPPTFSPALLVVTEGDNATFTCSFSNTSESFVLNWYRMSPSNQTDKLAAFPEDR
SQPGQDSRFRVTQLPNGRDFHMSVVRARRNDSGTYLCGAISLAPKAQIKESLRAEL
RVTERRAE
(SEQ ID NO:3)

FIG. 3A

ATGGCAAATCCTCCTACATTCTCCCCGGCACTGCTGGTTGTTACCGAAGGCGAT
AATGCGACCTTTACCTGTAGTTTCTCCAATACGAGCGAATCGTTTGTCCTGAACT
GGTATCGTATGAGCCCGTCTAATCAGACCGATAAACTGGCGGCCTTCCCGGAAG
ATCGCTCTCAGCCGGGCCAAGACAGCCGTTTTCGCGTTACGCAACTGCCGAACG
GTCGTGATTTCCATATGAGTGTGGTTCGCGCCCGTCGCAATGACTCCGGCACCT
ACCTGTGTGGTGCAATTTCACTGGCTCCGAAAGCCCAAATCAAAGAATCGCTGC
GTGCGGAACTGCGTGTTACCGAACGTCGTGCCGAA
(SEQ ID NO:4)

FIG. 3B

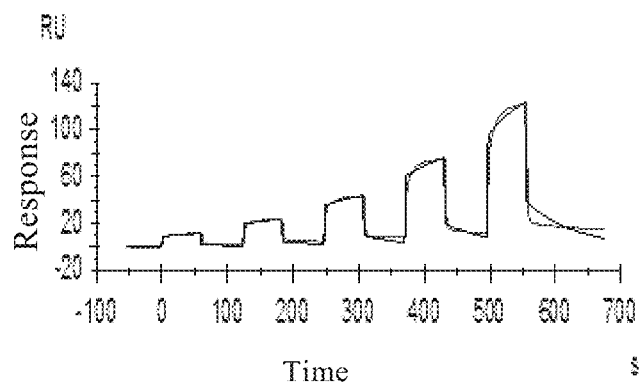

FIG. 4

FTVTVPKDLYVVEYGSNMTIECKFPVEKQLDLAALQVNWFMEDKNIIQFVHGEEDL
KVQHSSYRQRARLLKDQLSLGNAALQITDVKLQDAGVYVCLISYGGADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:5, L1C2)

FTVTVPKDLYVVEYGSNMTIECKFPVEKQLDLAALQVNWLMEDKNIIQFVHGEED
LKVQHSSYRQRARLLKDQLSLGNAALQITDVKLQDAGVYLCLISYGGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:6, L1F2)

WTVTVPKDLYVVEYGSNMTIECKFPVEKQLDLAALQVFWMMEDKNIIQFVHGEED
LKVQHSSYRQRARLLKDQLSLGNAALQITDVKLQDAGVYTCLISYGGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:7, L1A4)

FTVTVPKDLYVVEYGSNMTIECKFPVEKQLDLAALQVHWFMEDKNIPSFVHGEED
LKVQHSSYRQRARLLKDQLSLGNAALQITDVKLQDAGVYRCMISYGGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:8, L22A5)

FTVTVPKDLYVVEYGSNMTIECKFPVEKQLDLAALEVHWFMEDKNIVSFVHGEED
LKVQHSSYRQRARLLKDQLSLGNAALQITDVKLQDAGVYRCMISYGGADYKRITV
KVNAPYNKINQRIRVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:9, L2B6)

FIG. 5

FTVTVPKDLYVVEYGSNMTIECKFPVEKQLDLAAL<u>E</u>V<u>H</u>W<u>F</u>MEDKNI<u>FS</u>FVHGEEDL
KVQHSSYRQRARLLKDQLSLGNAALQITDVKLQDAGVYRCMISYGGADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:10, L2F4)

FTVTVPKDLYVVEYGSNMTIECKFPVEKQLDLAAL<u>E</u>V<u>H</u>W<u>F</u>MEDKNI<u>SS</u>FVHGEEDL
KVQHSSYRQRARLLKDQLSLGNAALQITDVKLQDAGVYRCMISYGGADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:11, L2F5)

FTVTVPKDLYVVEYGSNMTIECKFPVEKQLDLAAL<u>E</u>V<u>H</u>W<u>F</u>MEDKNI<u>LS</u>FVHGEEDL
KVQHSSYRQRARLLKDQLSLGNAALQITDVKLQDAGVYRCMISYGGADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL (SEQ ID NO:12, L2D7)

FTVTVPKDLYVVEYGSNMTIECKFPVEKQLDLAAL<u>Q</u>V<u>H</u>W<u>F</u>MEDKNI<u>LS</u>FVHGEED
LKVQHSSYRQRARLLKDQLSLGNAALQITDVKLQDAGVYRCMISYGGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:13, L2H3)

FTVTVPKDLYVVEYGSNMTIECKFPVEKQLDLAAL<u>Q</u>V<u>H</u>W<u>F</u>MEDKNI<u>Y</u>SFVHGEED
LKVQHSSYRQRARLLKDQLSLGNAALQITDVKLQDAGVYRCMISYGGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:14, L2G10)

FIG. 5 (CONT.)

FTVTVPKDLYVVEYGSNMTIECKFPVEKQLDLAAL<u>Q</u>V<u>H</u>W<u>W</u>MEDKNI<u>VS</u>FVHGEED
LKVQHSSYRQRARLLKDQLSLGNAALQITDVKLQDAGVYRCMISYGGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:15, L2C4)

FTVTVPKDLYVVEYGSNMTIECKFPVEKQLDLAAL<u>E</u>V<u>H</u>W<u>F</u>MEDKNI<u>IS</u>FVHGEEDL
KVQHSSYRQRARLLKDQLSLGNAALQITDVKLQDAGVYRCMISYGGADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:16, L22C7)

FTVTVPKDLYVVEYGSNMTIECKFPVEKQLDLAAL<u>Q</u>V<u>H</u>W<u>F</u>MEDKNI<u>VS</u>FVHGEED
LKVQHSSYRQRARLLKDQLSLGNAALQITDVKLQDAGVYRCMISYGGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:17, L2B8)

FTVTVPKDLYVVEYGSNMTIECKFPVEKQLDLAAL<u>Q</u>V<u>H</u>W<u>F</u>MEDKNI<u>FS</u>FVHGEED
LKVQHSSYRQRARLLKDQLSLGNAALQITDVKLQDAGVYRCMISYGGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:18, L22D5)

FTVTVPKDLYVVEYGSNMTIECKFPVEKQLDLAAL<u>Q</u>V<u>H</u>W<u>F</u>MEDKNI<u>AS</u>FVHGEED
LKVQHSSYRQRARLLKDQLSLGNAALQITDVKLQDAGVYRCMISYGGADYKRITV
KVNAPYNKINQRIRVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:19, L2A6)

FIG. 5 (CONT.)

FTVTVPKDLYVVEYGSNMTIECKFPVEKQLDLAALQVFWMMEDKNIIQFVHGEED
LKVQHSSYRQRARLLKDQLSLGNAALQITDVKLQDAGVYTCLIAYKGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:20, L3B3)

FTVTVPKDLYVVEYGSNMTIECKFPVEKQLDLAALQVFWMMEDKNIVSFVHGEED
LKVQHSSYRQRARLLKDQLSLGNAALQITDVKLQDAGVYTCLIAYKGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:21, L3B3a)

FTVTVPKDLYVVEYGSNMTIECKFPVEKQLDLAALQVFWMMEDKNIVSFVHGEED
LKVQHSSYRQRARLLKDQLSLGNAALQITDVKLQDAGVYVCLIAYKGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:22, L3B3b)

WTVTVPKDLYVVEYGSNMTIECKFPVEKQLDLAALQVFWMMEDKNIVSFVHGEE
DLKVQHSSYRQRARLLKDQLSLGNAALQITDVKLQDAGVYVCLIAYKGADYKRIT
VKVNAPYNKINQRILVVDPVTSEHELTCQAEGYPKAEVIWTSSDHQVLSGKTTTTN
SKREEKLFNVTSTLRINTTTNEIFYCTFRRLDPEENHTAELVIPEL
(SEQ ID NO:23, L3B3C)

WTVTVPKDLYVVEYGSNMTIECKFPVEKQLDLAALQVFWMMEDKNILSFVHGEED
LKVQHSSYRQRARLLKDQLSLGNAALQITDVKLQDAGVYVCLIAYKGADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:24, L3B3d)

FIG. 5 (CONT.)

FTVTVPKDLYVVEYGSNMTIECKFPVEKQLDLAAL<u>E</u>V<u>H</u>W<u>F</u>MEDKNIIQFVHGEEDL
KVQHSSYRQRARLLKDQLSLGNAALQITDVKLQDAGVY<u>TC</u>L<u>IG</u>Y<u>K</u>GADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:25, L3C7)

FTVTVPKDLYVVEYGSNMTIECKFPVEKQLDLAAL<u>E</u>V<u>H</u>W<u>F</u>MEDKNI<u>FS</u>FVHGEEDL
KVQHSSYRQRARLLKDQLSLGNAALQITDVKLQDAGVY<u>TC</u>L<u>IG</u>Y<u>K</u>GADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:26, L3C7a)

FTVTVPKDLYVVEYGSNMTIECKFPVEKQLDLAAL<u>E</u>V<u>H</u>W<u>F</u>MEDKNI<u>FS</u>FVHGEEDL
KVQHSSYRQRARLLKDQLSLGNAALQITDVKLQDAGVY<u>VC</u>L<u>IG</u>Y<u>K</u>GADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:27, L3C7b)

<u>W</u>TVTVPKDLYVVEYGSNMTIECKFPVEKQLDLAAL<u>E</u>V<u>H</u>W<u>F</u>MEDKNI<u>FS</u>FVHGEED
LKVQHSSYRQRARLLKDQLSLGNAALQITDVKLQDAGVY<u>TC</u>L<u>IG</u>Y<u>K</u>GADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:28, L3C7c)

<u>W</u>TVTVPKDLYVVEYGSNMTIECKFPVEKQLDLAAL<u>E</u>V<u>H</u>W<u>F</u>MEDKNI<u>FS</u>FVHGEED
LKVQHSSYRQRARLLKDQLSLGNAALQITDVKLQDAGVY<u>TC</u>L<u>IG</u>Y<u>K</u>G<u>G</u>ADYKRIT
VKVNAPYNKINQRILVVDPVTSEHELTCQAEGYPKAEVIWTSSDHQVLSGKTTTTN
SKREEKLFNVTSTLRINTTTNEIFYCTFRRLDPEENHTAELVIPEL
(SEQ ID NO:29, L3C7d)

FIG. 5 (CONT.)

FTVTVPKDLYVVEYGSNMTIECKFPVEKQLDLAAL<u>N</u>V<u>F</u>W<u>F</u>MEDKNIIQFVHGEEDL
KVQHSSYRQRARLLKDQLSLGNAALQITDVKLQDAGVY<u>TC</u>L<u>IG</u>Y<u>E</u>GADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:30, L3D9)

FTVTVPKDLYVVEYGSNMTIECKFPVEKQLDLAALIVYWEMEDKNIIQFVHGEEDL
KVQHSSYRQRARLLKDQLSLGNAALQITDVKLQDAGVY<u>TC</u>L<u>IG</u>Y<u>H</u>GADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:31, L32G5)

FTVTVPKDLYVVEYGSNMTIECKFPVEKQLDLAAL<u>TV</u>A<u>WY</u>MEDKNIIQFVHGEED
LKVQHSSYRQRARLLKDQLSLGNAALQITDVKLQDAGVY<u>TC</u>L<u>IG</u>Y<u>D</u>GADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:32, L3G10)

FTVTVPKDLYVVEYGSNMTIECKFPVEKQLDLAALIVYWEMEDKNIIQFVHGEEDL
KVQHSSYRQRARLLKDQLSLGNAALQITDVKLQDAGVY<u>TCMIA</u>YGGADYKRITVK
VNAPYNKINQRILVVDPVTSEHELTCQAEGYPKAEVIWTSSDHQVLSGKTTTTNSK
REEKLFNVTSTLRINTTTNEIFYCTFRRLDPEENHTAELVIPEL
(SEQ ID NO:33, L32H8)

FTVTVPKDLYVVEYGSNMTIECKFPVEKQLDLAALIVYWEMEDKNIIQFVHGEEDL
KVQHSSYRQRARLLKDQLSLGNAALQITDVKLQDAGVYRCMISYG<u>G</u>ADYKRITV
KVNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPEL
(SEQ ID NO:34, L4D6)

FIG. 5 (CONT.)

AQEVTQIPAALSVPEGENLVLNCSFTDSAIYNLQWFRQDPGKGLTSLLLITPWQREQ
TSGRLNASLDKSSGRSTLYIAASQPGDSATYLCAVRPLVDPTYIPTFGRGTSLIVHPY
IQNPDPAVYQLRDSKSSDKSVCLFTDFDSQTNVSQSKDSDVYITDKCVLDMRSMDF
KSNSAVAWSNKSDFACANAFNNSIIPEDT
(SEQ ID NO:35)

FIG. 6A

AIQMTQSPSSLSASVGDRVTITCRASQDIRNYLNWYQQKPGKAPKLLIYYTSRLESG
VPSRFSGSGSGTDYTLTISSLQPEDFATYYCQQGNTLPWTFGQGTKVEIKGGGGSGG
GGSGGGGSGGEVQLVESGGGLVQPGGSLRLSCAASGYSFTGYTMNWVRQAPGKG
LEWVALINPYKGVSTYNQKFKDRFTISVDKSKNTAYLQMNSLRAEDTAVYYCARS
GYYGDSDWYFDVWGQGTLVTVSSGGGGSNAGVTQTPKFQVLKTGQSMTLQCAQ
DMNHEYMSWYRQDPGMGLRLIHYSVAIQTTDQGEVPNGYNVSRSTTEDFPLRLLS
AAPSQTSVYFCASSYVGNTGELFFGEGSRLTVLEDLKNVFPPEVAVFEPSEAEISHT
QKATLVCLATGFYPDHVELSWWVNGKEVHSGVCTDPQPLKEQPALNDSRYALSSR
LRVSATFWQDPRNHFRCQVQFYGLSENDEWTQDRAKPVTQIVSAEAWGRAD
(SEQ ID NO:36)

FIG. 6B

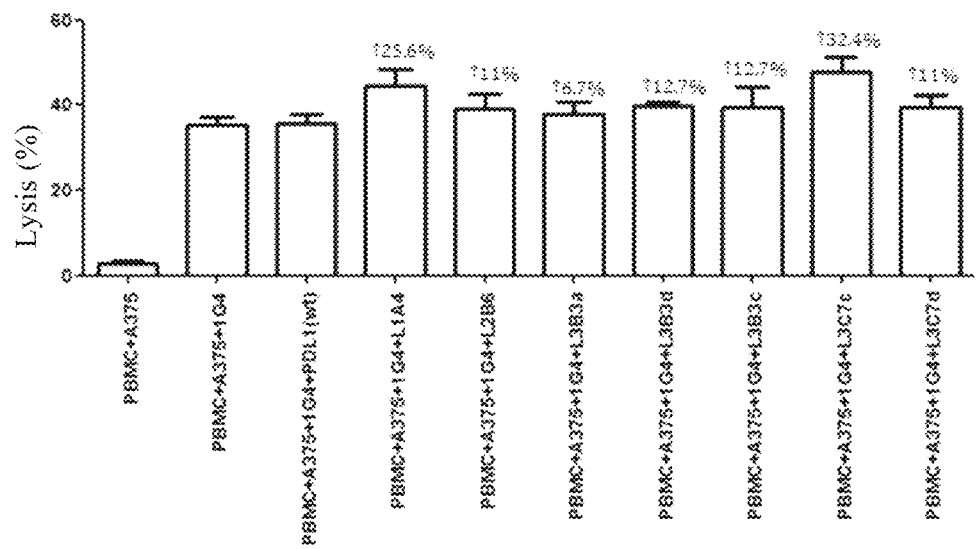

FIG. 7

SKYGPPCPSCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSLSL
SLGK
(SEQ ID NO:37, hIgG4Fc)

FIG. 8A

TCAAAGTATGGACCACCTTGCCCATCCTGTCCAGCACCAGAGTTTCTGGGCGGA
CCCTCCGTGTTCCTGTTTCCACCCAAGCCTAAAGATACACTGATGATTTCCCGCA
CACCTGAAGTCACTTGCGTGGTCGTGGACGTGAGCCAGGAGGATCCAGAAGTCC
AGTTCAACTGGTACGTGGACGGAGTCGAGGTGCACAATGCCAAGACCAAACCC
CGGGAGGAACAGTTTAACAGTACATACAGAGTCGTGTCAGTCCTGACTGTGCTG
CATCAGGACTGGCTGAACGGCAAGGAGTATAAGTGCAAAGTGTCTAATAAGGG
ACTGCCTTCATCCATCGAGAAACAATTAGTAAGGCAAAAGGCCAGCCTAGAG
AACCACAGGTGTACACTCTGCCTCCAAGTCAGGAGGAAATGACTAAGAACCAG
GTCTCACTGACCTGTCTGGTGAAAGGGTTCTATCCAAGCGATATCGCTGTGGAG
TGGGAATCTAATGGTCAGCCCGAGAACAATTACAAGACAACTCCCCCTGTGCTG
GACAGCGATGGCTCTTTCTTTCTGTATTCCCGTCTGACTGTGGACAAGAGCAGGT
GGCAGGAGGGAAACGTCTTTAGCTGTTCTGTGATGCACGAAGCTCTGCACAATC
ATTACACCCAGAAGAGTCTGTCACTGTCCCTGGGCAAA
(SEQ ID NO:38, hIgG4Fc)

FIG. 8B

SEQUENCE LISTING

```
<160> NUMBER OF SEQ ID NOS: 36

<210> SEQ ID NO 1
<211> LENGTH: 211
<212> TYPE: PRT
<213> ORGANISM: Homo sapiens

<400> SEQUENCE: 1

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
```

Pro Glu Leu
    210

<210> SEQ ID NO 2
<211> LENGTH: 633
<212> TYPE: DNA
<213> ORGANISM: Homo sapiens

<400> SEQUENCE: 2
tttacggtta cggttccgaa agacctgtat gtggttgaat acggctctaa tatgacgatt      60
gaatgcaaat tcccggttga aaaacaactg gatctggcgg ccctgattgt gtattgggaa     120
atggaagaca aaacatcat ccaattcgtg catggcgaag aagatctgaa agttcagcac     180
agctcttacc gtcaacgcgc acgtctgctg aaagaccagc tgagcctggg caatgcagct     240
ctgcagatca cggatgttaa actgcaagac gccggtgtct atcgctgcat gatttcttat     300
ggcggtgcag actacaaacg tatcaccgtc aaagtgaacg ctccgtacaa caaaattaat     360
cagcgcatcc tggtggttga tccggttacg tccgaacatg aactgacctg tcaagcggaa     420
ggctatccga agccgaagt catttggacc agttccgatc accaggtgct gtcaggtaaa     480
accacgacca cgaactcgaa acgcgaagaa aaactgttta atgtcacgag caccctgcgt     540
attaacacca cgaccaatga aatcttctac tgcacctttc gtcgtctgga cccggaagaa     600
aatcatacgg cggaactggt tatcccggaa ctg                                  633

<210> SEQ ID NO 3
<211> LENGTH: 120
<212> TYPE: PRT
<213> ORGANISM: Homo sapiens

<400> SEQUENCE: 3

Met Ala Asn Pro Pro Thr Phe Ser Pro Ala Leu Leu Val Val Thr Glu
1               5                   10                  15

Gly Asp Asn Ala Thr Phe Thr Cys Ser Phe Ser Asn Thr Ser Glu Ser
            20                  25                  30

Phe Val Leu Asn Trp Tyr Arg Met Ser Pro Ser Asn Gln Thr Asp Lys
        35                  40                  45

Leu Ala Ala Phe Pro Glu Asp Arg Ser Gln Pro Gly Gln Asp Ser Arg
    50                  55                  60

Phe Arg Val Thr Gln Leu Pro Asn Gly Arg Asp Phe His Met Ser Val
65                  70                  75                  80

Val Arg Ala Arg Arg Asn Asp Ser Gly Thr Tyr Leu Cys Gly Ala Ile
                85                  90                  95

Ser Leu Ala Pro Lys Ala Gln Ile Lys Glu Ser Leu Arg Ala Glu Leu
            100                 105                 110

Arg Val Thr Glu Arg Arg Ala Glu
        115                 120

<210> SEQ ID NO 4
<211> LENGTH: 360
<212> TYPE: DNA
<213> ORGANISM: Homo sapiens

<400> SEQUENCE: 4
atggcaaatc ctcctacatt ctccccggca ctgctggttg ttaccgaagg cgataatgcg      60
acctttacct gtagtttctc caatacgagc gaatcgtttg tcctgaactg gtatcgtatg     120

```
agcccgtcta atcagaccga taaactggcg gccttcccgg aagatcgctc tcagccgggc    180
caagacagcc gttttcgcgt tacgcaactg ccgaacggtc gtgatttcca tatgagtgtg    240
gttcgcgccc gtcgcaatga ctccggcacc tacctgtgtg gtgcaatttc actggctccg    300
aaagcccaaa tcaaagaatc gctgcgtgcg gaactgcgtg ttaccgaacg tcgtgccgaa    360
```

<210> SEQ ID NO 5
<211> LENGTH: 211
<212> TYPE: PRT
<213> ORGANISM: Artificial sequence
<220> FEATURE:
<223> OTHER INFORMATION: polypeptide

<400> SEQUENCE: 5

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Gln Val Asn Trp Phe Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Val Cys
                85                  90                  95

Leu Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu
    210
```

<210> SEQ ID NO 6
<211> LENGTH: 211
<212> TYPE: PRT
<213> ORGANISM: Artificial sequence
<220> FEATURE:
<223> OTHER INFORMATION: polypeptide

<400> SEQUENCE: 6

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Gln Val Asn Trp Leu Met Glu Asp Lys Asn Ile Ile Gln
        35                  40                  45
```

```
Phe Val His Gly Glu Glu Asp Leu Lys Val Gln His Ser Ser Tyr Arg
     50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Leu Cys
                 85                  90                  95

Leu Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                    165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu
    210

<210> SEQ ID NO 7
<211> LENGTH: 211
<212> TYPE: PRT
<213> ORGANISM: Artificial sequence
<220> FEATURE:
<223> OTHER INFORMATION: polypeptide

<400> SEQUENCE: 7

Trp Thr Val Thr Val Pro Lys Asp Leu Tyr Val Val Glu Tyr Gly Ser
 1               5                  10                  15

Asn Met Thr Ile Glu Cys Lys Phe Pro Val Glu Lys Gln Leu Asp Leu
                 20                  25                  30

Ala Ala Leu Gln Val Phe Trp Met Met Glu Asp Lys Asn Ile Ile Gln
             35                  40                  45

Phe Val His Gly Glu Glu Asp Leu Lys Val Gln His Ser Ser Tyr Arg
     50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Thr Cys
                 85                  90                  95

Leu Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                    165                 170                 175

Ser Thr Leu Arg Ile Asn Thr Thr Thr Asn Glu Ile Phe Tyr Cys Thr
                180                 185                 190
```

```
Phe Arg Arg Leu Asp Pro Glu Glu Asn His Thr Ala Glu Leu Val Ile
            195                 200                 205
Pro Glu Leu
    210

<210> SEQ ID NO 8
<211> LENGTH: 211
<212> TYPE: PRT
<213> ORGANISM: Artificial sequence
<220> FEATURE:
<223> OTHER INFORMATION: polypeptide

<400> SEQUENCE: 8

Phe Thr Val Thr Val Pro Lys Asp Leu Tyr Val Val Glu Tyr Gly Ser
1               5                   10                  15
Asn Met Thr Ile Glu Cys Lys Phe Pro Val Glu Lys Gln Leu Asp Leu
            20                  25                  30
Ala Ala Leu Gln Val His Trp Phe Met Glu Asp Lys Asn Ile Pro Ser
        35                  40                  45
Phe Val His Gly Glu Glu Asp Leu Lys Val Gln His Ser Ser Tyr Arg
    50                  55                  60
Gln Arg Ala Arg Leu Leu Lys Asp Gln Leu Ser Leu Gly Asn Ala Ala
65                  70                  75                  80
Leu Gln Ile Thr Asp Val Lys Leu Gln Asp Ala Gly Val Tyr Arg Cys
                85                  90                  95
Met Ile Ser Tyr Gly Gly Ala Asp Tyr Lys Arg Ile Thr Val Lys Val
            100                 105                 110
Asn Ala Pro Tyr Asn Lys Ile Asn Gln Arg Ile Leu Val Val Asp Pro
        115                 120                 125
Val Thr Ser Glu His Glu Leu Thr Cys Gln Ala Glu Gly Tyr Pro Lys
    130                 135                 140
Ala Glu Val Ile Trp Thr Ser Ser Asp His Gln Val Leu Ser Gly Lys
145                 150                 155                 160
Thr Thr Thr Thr Asn Ser Lys Arg Glu Glu Lys Leu Phe Asn Val Thr
                165                 170                 175
Ser Thr Leu Arg Ile Asn Thr Thr Asn Glu Ile Phe Tyr Cys Thr
            180                 185                 190
Phe Arg Arg Leu Asp Pro Glu Glu Asn His Thr Ala Glu Leu Val Ile
        195                 200                 205
Pro Glu Leu
    210

<210> SEQ ID NO 9
<211> LENGTH: 211
<212> TYPE: PRT
<213> ORGANISM: Artificial sequence
<220> FEATURE:
<223> OTHER INFORMATION: polypeptide

<400> SEQUENCE: 9

Phe Thr Val Thr Val Pro Lys Asp Leu Tyr Val Val Glu Tyr Gly Ser
1               5                   10                  15
Asn Met Thr Ile Glu Cys Lys Phe Pro Val Glu Lys Gln Leu Asp Leu
            20                  25                  30
Ala Ala Leu Glu Val His Trp Phe Met Glu Asp Lys Asn Ile Val Ser
        35                  40                  45
Phe Val His Gly Glu Glu Asp Leu Lys Val Gln His Ser Ser Tyr Arg
    50                  55                  60
```

```
Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
             85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Arg Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu
    210

<210> SEQ ID NO 10
<211> LENGTH: 211
<212> TYPE: PRT
<213> ORGANISM: Artificial sequence
<220> FEATURE:
<223> OTHER INFORMATION: polypeptide

<400> SEQUENCE: 10

Phe Thr Val Thr Val Pro Lys Asp Leu Tyr Val Val Glu Tyr Gly Ser
  1               5                  10                  15

Asn Met Thr Ile Glu Cys Lys Phe Pro Val Glu Lys Gln Leu Asp Leu
             20                  25                  30

Ala Ala Leu Glu Val His Trp Phe Met Glu Asp Lys Asn Ile Phe Ser
         35                  40                  45

Phe Val His Gly Glu Glu Asp Leu Lys Val Gln His Ser Ser Tyr Arg
 50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
             85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205
```

Pro Glu Leu
    210

<210> SEQ ID NO 11
<211> LENGTH: 211
<212> TYPE: PRT
<213> ORGANISM: Artificial sequence
<220> FEATURE:
<223> OTHER INFORMATION: polypeptide

<400> SEQUENCE: 11

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Glu Val His Trp Phe Met Glu Asp Lys Asn Ile Ser Ser
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu
    210

<210> SEQ ID NO 12
<211> LENGTH: 211
<212> TYPE: PRT
<213> ORGANISM: Artificial sequence
<220> FEATURE:
<223> OTHER INFORMATION: polypeptide

<400> SEQUENCE: 12

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Glu Val His Trp Phe Met Glu Asp Lys Asn Ile Leu Ser
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala

```
                65                  70                  75                  80
Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
                115                 120                 125

Val Thr Ser Glu His Glu Leu Thr Cys Gln Ala Glu Gly Tyr Pro Lys
                130                 135                 140

Ala Glu Val Ile Trp Thr Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu
210

<210> SEQ ID NO 13
<211> LENGTH: 211
<212> TYPE: PRT
<213> ORGANISM: Artificial sequence
<220> FEATURE:
<223> OTHER INFORMATION: polypeptide

<400> SEQUENCE: 13

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Gln Val His Trp Phe Met Glu Asp Lys Asn Ile Leu Ser
                35                  40                  45

Phe Val His Gly Glu Glu Asp Leu Lys Val Gln His Ser Ser Tyr Arg
                50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
                115                 120                 125

Val Thr Ser Glu His Glu Leu Thr Cys Gln Ala Glu Gly Tyr Pro Lys
                130                 135                 140

Ala Glu Val Ile Trp Thr Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu
```

```
<210> SEQ ID NO 14
<211> LENGTH: 211
<212> TYPE: PRT
<213> ORGANISM: Artificial sequence
<220> FEATURE:
<223> OTHER INFORMATION: polypeptide

<400> SEQUENCE: 14

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Gln Val His Trp Phe Met Glu Asp Lys Asn Ile Tyr Ser
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu
    210

<210> SEQ ID NO 15
<211> LENGTH: 211
<212> TYPE: PRT
<213> ORGANISM: Artificial sequence
<220> FEATURE:
<223> OTHER INFORMATION: polypeptide

<400> SEQUENCE: 15

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Gln Val His Trp Trp Met Glu Asp Lys Asn Ile Val Ser
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80
```

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
            130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu
    210

<210> SEQ ID NO 16
<211> LENGTH: 211
<212> TYPE: PRT
<213> ORGANISM: Artificial sequence
<220> FEATURE:
<223> OTHER INFORMATION: polypeptide

<400> SEQUENCE: 16

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Glu Val His Trp Phe Met Glu Asp Lys Asn Ile Ile Ser
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
            130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu
    210

```
<210> SEQ ID NO 17
<211> LENGTH: 211
<212> TYPE: PRT
<213> ORGANISM: Artificial sequence
<220> FEATURE:
<223> OTHER INFORMATION: polypeptide

<400> SEQUENCE: 17

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Gln Val His Trp Phe Met Glu Asp Lys Asn Ile Val Ser
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu
    210

<210> SEQ ID NO 18
<211> LENGTH: 211
<212> TYPE: PRT
<213> ORGANISM: Artificial sequence
<220> FEATURE:
<223> OTHER INFORMATION: polypeptide

<400> SEQUENCE: 18

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Gln Val His Trp Phe Met Glu Asp Lys Asn Ile Phe Ser
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95
```

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
            130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu
    210

<210> SEQ ID NO 19
<211> LENGTH: 211
<212> TYPE: PRT
<213> ORGANISM: Artificial sequence
<220> FEATURE:
<223> OTHER INFORMATION: polypeptide

<400> SEQUENCE: 19

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Gln Val His Trp Phe Met Glu Asp Lys Asn Ile Ala Ser
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Arg Val Val Asp Pro
            115                 120                 125

Val Thr Ser Glu His Glu Leu Thr Cys Gln Ala Glu Gly Tyr Pro Lys
            130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu
    210

<210> SEQ ID NO 20

```
<211> LENGTH: 211
<212> TYPE: PRT
<213> ORGANISM: Artificial sequence
<220> FEATURE:
<223> OTHER INFORMATION: polypeptide

<400> SEQUENCE: 20

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Gln Val Phe Trp Met Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Thr Cys
                85                  90                  95

Leu Ile Ala Tyr Lys Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu
    210

<210> SEQ ID NO 21
<211> LENGTH: 211
<212> TYPE: PRT
<213> ORGANISM: Artificial sequence
<220> FEATURE:
<223> OTHER INFORMATION: polypeptide

<400> SEQUENCE: 21

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Gln Val Phe Trp Met Met Glu Asp Lys Asn Ile Val Ser
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Thr Cys
                85                  90                  95

Leu Ile Ala Tyr Lys Gly Ala Asp Tyr Lys Arg Ile Thr Val Lys Val
```

```
                    100                 105                 110
Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu
        210

<210> SEQ ID NO 22
<211> LENGTH: 211
<212> TYPE: PRT
<213> ORGANISM: Artificial sequence
<220> FEATURE:
<223> OTHER INFORMATION: polypeptide

<400> SEQUENCE: 22

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Gln Val Phe Trp Met Met Glu Asp Lys Asn Ile Val Ser
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Val Cys
                85                  90                  95

Leu Ile Ala Tyr Lys Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu
        210

<210> SEQ ID NO 23
<211> LENGTH: 211
<212> TYPE: PRT
```

<213> ORGANISM: Artificial sequence
<220> FEATURE:
<223> OTHER INFORMATION: polypeptide

<400> SEQUENCE: 23

```
Trp Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Gln Val Phe Trp Met Met Glu Asp Lys Asn Ile Val Ser
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Val Cys
                85                  90                  95

Leu Ile Ala Tyr Lys Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu
    210
```

<210> SEQ ID NO 24
<211> LENGTH: 211
<212> TYPE: PRT
<213> ORGANISM: Artificial sequence
<220> FEATURE:
<223> OTHER INFORMATION: polypeptide

<400> SEQUENCE: 24

```
Trp Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Gln Val Phe Trp Met Met Glu Asp Lys Asn Ile Leu Ser
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Val Cys
                85                  90                  95

Leu Ile Ala Tyr Lys Gly Ala Asp Tyr Lys Arg Ile Thr Val Lys Val
            100                 105                 110
```

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu
    210

<210> SEQ ID NO 25
<211> LENGTH: 211
<212> TYPE: PRT
<213> ORGANISM: Artificial sequence
<220> FEATURE:
<223> OTHER INFORMATION: polypeptide

<400> SEQUENCE: 25

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Glu Val His Trp Phe Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Thr Cys
                85                  90                  95

Leu Ile Gly Tyr Lys Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu
    210

<210> SEQ ID NO 26
<211> LENGTH: 211
<212> TYPE: PRT
<213> ORGANISM: Artificial sequence
<220> FEATURE:

<223> OTHER INFORMATION: polypeptide

<400> SEQUENCE: 26

```
Phe Thr Val Thr Val Pro Lys Asp Leu Tyr Val Val Glu Tyr Gly Ser
1               5                   10                  15
Asn Met Thr Ile Glu Cys Lys Phe Pro Val Glu Lys Gln Leu Asp Leu
            20                  25                  30
Ala Ala Leu Glu Val His Trp Phe Met Glu Asp Lys Asn Ile Phe Ser
        35                  40                  45
Phe Val His Gly Glu Glu Asp Leu Lys Val Gln His Ser Ser Tyr Arg
    50                  55                  60
Gln Arg Ala Arg Leu Leu Lys Asp Gln Leu Ser Leu Gly Asn Ala Ala
65                  70                  75                  80
Leu Gln Ile Thr Asp Val Lys Leu Gln Asp Ala Gly Val Tyr Thr Cys
                85                  90                  95
Leu Ile Gly Tyr Lys Gly Ala Asp Tyr Lys Arg Ile Thr Val Lys Val
            100                 105                 110
Asn Ala Pro Tyr Asn Lys Ile Asn Gln Arg Ile Leu Val Val Asp Pro
        115                 120                 125
Val Thr Ser Glu His Glu Leu Thr Cys Gln Ala Glu Gly Tyr Pro Lys
    130                 135                 140
Ala Glu Val Ile Trp Thr Ser Ser Asp His Gln Val Leu Ser Gly Lys
145                 150                 155                 160
Thr Thr Thr Thr Asn Ser Lys Arg Glu Glu Lys Leu Phe Asn Val Thr
                165                 170                 175
Ser Thr Leu Arg Ile Asn Thr Thr Asn Glu Ile Phe Tyr Cys Thr
            180                 185                 190
Phe Arg Arg Leu Asp Pro Glu Glu Asn His Thr Ala Glu Leu Val Ile
        195                 200                 205
Pro Glu Leu
    210
```

<210> SEQ ID NO 27
<211> LENGTH: 211
<212> TYPE: PRT
<213> ORGANISM: Artificial sequence
<220> FEATURE:
<223> OTHER INFORMATION: polypeptide

<400> SEQUENCE: 27

```
Phe Thr Val Thr Val Pro Lys Asp Leu Tyr Val Val Glu Tyr Gly Ser
1               5                   10                  15
Asn Met Thr Ile Glu Cys Lys Phe Pro Val Glu Lys Gln Leu Asp Leu
            20                  25                  30
Ala Ala Leu Glu Val His Trp Phe Met Glu Asp Lys Asn Ile Phe Ser
        35                  40                  45
Phe Val His Gly Glu Glu Asp Leu Lys Val Gln His Ser Ser Tyr Arg
    50                  55                  60
Gln Arg Ala Arg Leu Leu Lys Asp Gln Leu Ser Leu Gly Asn Ala Ala
65                  70                  75                  80
Leu Gln Ile Thr Asp Val Lys Leu Gln Asp Ala Gly Val Tyr Val Cys
                85                  90                  95
Leu Ile Gly Tyr Lys Gly Ala Asp Tyr Lys Arg Ile Thr Val Lys Val
            100                 105                 110
Asn Ala Pro Tyr Asn Lys Ile Asn Gln Arg Ile Leu Val Val Asp Pro
        115                 120                 125
```

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu
    210

<210> SEQ ID NO 28
<211> LENGTH: 211
<212> TYPE: PRT
<213> ORGANISM: Artificial sequence
<220> FEATURE:
<223> OTHER INFORMATION: polypeptide

<400> SEQUENCE: 28

Trp Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Glu Val His Trp Phe Met Glu Asp Lys Asn Ile Phe Ser
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Thr Cys
                85                  90                  95

Leu Ile Gly Tyr Lys Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu
    210

<210> SEQ ID NO 29
<211> LENGTH: 212
<212> TYPE: PRT
<213> ORGANISM: Artificial sequence
<220> FEATURE:
<223> OTHER INFORMATION: polypeptide

```
<400> SEQUENCE: 29

Trp Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Glu Val His Trp Phe Met Glu Asp Lys Asn Ile Phe Ser
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Thr Cys
            85                  90                  95

Leu Ile Gly Tyr Lys Gly Gly Ala Asp Tyr Lys Arg Ile Thr Val Lys
            100                 105                 110

Val Asn Ala Pro Tyr Asn Lys Ile Asn Gln Arg Ile Leu Val Val Asp
            115                 120                 125

Pro Val Thr Ser Glu His Glu Leu Thr Cys Gln Ala Glu Gly Tyr Pro
130                 135                 140

Lys Ala Glu Val Ile Trp Thr Ser Ser Asp His Gln Val Leu Ser Gly
145                 150                 155                 160

Lys Thr Thr Thr Thr Asn Ser Lys Arg Glu Glu Lys Leu Phe Asn Val
                165                 170                 175

Thr Ser Thr Leu Arg Ile Asn Thr Thr Thr Asn Glu Ile Phe Tyr Cys
            180                 185                 190

Thr Phe Arg Arg Leu Asp Pro Glu Glu Asn His Thr Ala Glu Leu Val
        195                 200                 205

Ile Pro Glu Leu
    210

<210> SEQ ID NO 30
<211> LENGTH: 211
<212> TYPE: PRT
<213> ORGANISM: Artificial sequence
<220> FEATURE:
<223> OTHER INFORMATION: polypeptide

<400> SEQUENCE: 30

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Asn Val Phe Trp Phe Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Thr Cys
            85                  90                  95

Leu Ile Gly Tyr Glu Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
```

```
                    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                    165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu
        210

<210> SEQ ID NO 31
<211> LENGTH: 211
<212> TYPE: PRT
<213> ORGANISM: Artificial sequence
<220> FEATURE:
<223> OTHER INFORMATION: polypeptide

<400> SEQUENCE: 31

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Thr Cys
                85                  90                  95

Leu Ile Gly Tyr His Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                    165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu
        210

<210> SEQ ID NO 32
<211> LENGTH: 211
<212> TYPE: PRT
<213> ORGANISM: Artificial sequence
<220> FEATURE:
<223> OTHER INFORMATION: polypeptide

<400> SEQUENCE: 32
```

```
Phe Thr Val Thr Val Pro Lys Asp Leu Tyr Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Thr Val Ala Trp Tyr Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Thr Cys
            85                  90                  95

Leu Ile Gly Tyr Asp Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu
    210

<210> SEQ ID NO 33
<211> LENGTH: 211
<212> TYPE: PRT
<213> ORGANISM: Artificial sequence
<220> FEATURE:
<223> OTHER INFORMATION: polypeptide

<400> SEQUENCE: 33

Phe Thr Val Thr Val Pro Lys Asp Leu Tyr Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Thr Cys
            85                  90                  95

Met Ile Ala Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140
```

```
Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu
    210

<210> SEQ ID NO 34
<211> LENGTH: 212
<212> TYPE: PRT
<213> ORGANISM: Artificial sequence
<220> FEATURE:
<223> OTHER INFORMATION: polypeptide

<400> SEQUENCE: 34

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys
            100                 105                 110

Val Asn Ala Pro Tyr Asn Lys Ile Asn Gln Arg Ile Leu Val Val Asp
        115                 120                 125

Pro Val Thr Ser Glu His Glu Leu Thr Cys Gln Ala Glu Gly Tyr Pro
    130                 135                 140

Lys Ala Glu Val Ile Trp Thr Ser Ser Asp His Gln Val Leu Ser Gly
145                 150                 155                 160

Lys Thr Thr Thr Thr Asn Ser Lys Arg Glu Glu Lys Leu Phe Asn Val
                165                 170                 175

Thr Ser Thr Leu Arg Ile Asn Thr Thr Thr Asn Glu Ile Phe Tyr Cys
            180                 185                 190

Thr Phe Arg Arg Leu Asp Pro Glu Glu Asn His Thr Ala Glu Leu Val
        195                 200                 205

Ile Pro Glu Leu
    210

<210> SEQ ID NO 35
<211> LENGTH: 200
<212> TYPE: PRT
<213> ORGANISM: Artificial sequence
<220> FEATURE:
<223> OTHER INFORMATION: polypeptide

<400> SEQUENCE: 35

Ala Gln Glu Val Thr Gln Ile Pro Ala Ala Leu Ser Val Pro Glu Gly
1               5                   10                  15
```

```
Glu Asn Leu Val Leu Asn Cys Ser Phe Thr Asp Ser Ala Ile Tyr Asn
             20                  25                  30

Leu Gln Trp Phe Arg Gln Asp Pro Gly Lys Gly Leu Thr Ser Leu Leu
         35                  40                  45

Leu Ile Thr Pro Trp Gln Arg Glu Gln Thr Ser Gly Arg Leu Asn Ala
     50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Leu Val
                 85                  90                  95

Asp Pro Thr Tyr Ile Pro Thr Phe Gly Arg Gly Thr Ser Leu Ile Val
             100                 105                 110

His Pro Tyr Ile Gln Asn Pro Asp Pro Ala Val Tyr Gln Leu Arg Asp
         115                 120                 125

Ser Lys Ser Ser Asp Lys Ser Val Cys Leu Phe Thr Asp Phe Asp Ser
130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                 165                 170                 175

Val Ala Trp Ser Asn Lys Ser Asp Phe Ala Cys Ala Asn Ala Phe Asn
             180                 185                 190

Asn Ser Ile Ile Pro Glu Asp Thr
         195                 200

<210> SEQ ID NO 36
<211> LENGTH: 494
<212> TYPE: PRT
<213> ORGANISM: Artificial sequence
<220> FEATURE:
<223> OTHER INFORMATION: polypeptide

<400> SEQUENCE: 36

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Glu Ser Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Val Glu Ile Lys Gly Gly Gly Gly Ser
             100                 105                 110

Gly Gly Gly Gly Ser Gly Gly Gly Ser Gly Gly Glu Val Gln Leu
         115                 120                 125

Val Glu Ser Gly Gly Gly Leu Val Gln Pro Gly Gly Ser Leu Arg Leu
130                 135                 140

Ser Cys Ala Ala Ser Gly Tyr Ser Phe Thr Gly Tyr Thr Met Asn Trp
145                 150                 155                 160

Val Arg Gln Ala Pro Gly Lys Gly Leu Glu Trp Val Ala Leu Ile Asn
                 165                 170                 175
```

-continued

```
Pro Tyr Lys Gly Val Ser Thr Tyr Asn Gln Lys Phe Lys Asp Arg Phe
            180                 185                 190

Thr Ile Ser Val Asp Lys Ser Lys Asn Thr Ala Tyr Leu Gln Met Asn
        195                 200                 205

Ser Leu Arg Ala Glu Asp Thr Ala Val Tyr Tyr Cys Ala Arg Ser Gly
    210                 215                 220

Tyr Tyr Gly Asp Ser Asp Trp Tyr Phe Asp Val Trp Gly Gln Gly Thr
225                 230                 235                 240

Leu Val Thr Val Ser Ser Gly Gly Gly Ser Asn Ala Gly Val Thr
                245                 250                 255

Gln Thr Pro Lys Phe Gln Val Leu Lys Thr Gly Gln Ser Met Thr Leu
            260                 265                 270

Gln Cys Ala Gln Asp Met Asn His Glu Tyr Met Ser Trp Tyr Arg Gln
            275                 280                 285

Asp Pro Gly Met Gly Leu Arg Leu Ile His Tyr Ser Val Ala Ile Gln
        290                 295                 300

Thr Thr Asp Gln Gly Glu Val Pro Asn Gly Tyr Asn Val Ser Arg Ser
305                 310                 315                 320

Thr Thr Glu Asp Phe Pro Leu Arg Leu Leu Ser Ala Ala Pro Ser Gln
                325                 330                 335

Thr Ser Val Tyr Phe Cys Ala Ser Ser Tyr Val Gly Asn Thr Gly Glu
            340                 345                 350

Leu Phe Phe Gly Glu Gly Ser Arg Leu Thr Val Leu Glu Asp Leu Lys
            355                 360                 365

Asn Val Phe Pro Pro Glu Val Ala Val Phe Glu Pro Ser Glu Ala Glu
        370                 375                 380

Ile Ser His Thr Gln Lys Ala Thr Leu Val Cys Leu Ala Thr Gly Phe
385                 390                 395                 400

Tyr Pro Asp His Val Glu Leu Ser Trp Trp Val Asn Gly Lys Glu Val
                405                 410                 415

His Ser Gly Val Cys Thr Asp Pro Gln Pro Leu Lys Glu Gln Pro Ala
            420                 425                 430

Leu Asn Asp Ser Arg Tyr Ala Leu Ser Ser Arg Leu Arg Val Ser Ala
        435                 440                 445

Thr Phe Trp Gln Asp Pro Arg Asn His Phe Arg Cys Gln Val Gln Phe
        450                 455                 460

Tyr Gly Leu Ser Glu Asn Asp Glu Trp Thr Gln Asp Arg Ala Lys Pro
465                 470                 475                 480

Val Thr Gln Ile Val Ser Ala Glu Ala Trp Gly Arg Ala Asp
                485                 490
```

HIGH-AFFINITY AND SOLUBLE PDL-1 MOLECULE

CROSS-REFERENCE TO RELATED APPLICATIONS

This application is a national phase application under 35 U.S.C. 371 claiming priority to PCT/CN2016/101597, filed Oct. 9, 2016, which application claims priority to CN 201510653647.9, filed Oct. 10, 2015, the teachings of which are hereby incorporated by reference in their entireties for all purposes.

TECHNICAL FIELD

The present invention relates to the field of biotechnology. More specifically, the present invention relates to a soluble Programmed Death Ligand-1 (PDL-1) molecule with high affinity towards Programmed Death-1 (PD-1) molecule, and preparation method and use thereof.

BACKGROUND TECHNIQUE

PD-1 is an immuno-inhibitory receptor expressed on activated T cells and B cells. PDL-1 is a ligand for PD-1 and belongs to the B7 family. PDL-1 has IgV and IgC-like domain, transmembrane domain and cytoplasmic tail domain. PDL-1 interacts with receptor PD-1 on lymphocytes and plays an important role in the negative regulation of immune responses. Many tumor cell lines and tumor cells highly express PDL-1 molecules (Konishi J et al., Clin. Cancer Res., 2004, 10(15): 5094-5100), which bind to PD-1 molecules on the surface of lymphocytes and weaken the anti-tumor immune response of body (Radziewicz H et al., J Virol, 2007, 81(6): 2545-2553), thereby resulting in occurrence of tumor immune escape. It is found in the study that, nearly half of CD8+ T cells infiltrating into tumors express PD-1 molecules in cervical cancer and liver cancer. The binding of PD-1 molecule to PDL-1 expressed by tumor cells may lead to depletion and apoptosis of CTL cells (Dong H et al., J Mol Med (Berl), 2003, 81(5):281-287; Karim R et al., Clin Cancer Res, 2009, 15(20): 6341-6347; Zhao Q et al., Eur J Immunol, 2011, 41(8):2314-2322).

For the tumor immune escape problem mentioned above, blocking interaction between PD-1 on the surface of lymphocytes and PDL-1 on the surface of tumor cells can increase the immunity of lymphocytes, and thus help to clear tumor cells by the immune system. A lot of researches have been done focusing on this problem. T. Nomi et al. (Clin. Cancer Res. 13:2151-2157 (2007)) demonstrated the therapeutic efficacy of blocking the interaction of PD-1 with PDL-1 in a mouse model of invasive pancreatic cancer. The skilled in the art are dedicated to studying the interaction between PDL-1 and PD-1 in order to find an effective way to increase the killing capacity of lymphocytes.

SUMMARY OF THE INVENTION

The object of the present invention is to provide a PDL-1 molecule having a high affinity for PD-1 molecules.

Another object of the present invention is to provide a preparation method and use of the PDL-1 molecule with high affinity mentioned above.

In the first aspect of the present invention, it provides a PDL-1 molecule which contains a mutation in the amino acid sequence as shown in SEQ ID NO: 1.

In another preferred embodiment, the amino acid sequence of the PDL-1 molecule is based on the amino acid sequence as shown in SEQ ID NO.:1, and a mutation in one or more amino acid residues or insertion of an amino acid residue is performed on the amino acid sequence as shown in SEQ ID NO: 1 to obtain the PDL-1 molecule.

In another preferred embodiment, the amino acid sequence of the PDL-1 molecule has at least 90% (preferably, at least 92%; and more preferably, at least 94%) sequence identity with the amino acid sequence as shown in SEQ ID NO: 1.

In another preferred embodiment, the affinity of the PDL-1 molecule to the PD-1 molecule is at least 2 folds; preferably, at least 5 folds; more preferably, at least 10 folds; most preferably, at least 50 folds of the affinity of the wild-type PDL-1 molecule to the PD-1 molecule.

In another preferred embodiment, the affinity of the PDL-1 molecule to the PD-1 molecule is at least 100 folds; preferably, at least 200 folds; and more preferably, at least 500 folds of the affinity of the wild-type PDL-1 molecule to the PD-1 molecule.

In another preferred embodiment, the mutated amino acid residue site in the PDL-1 molecule is one or more amino acid residues in position 1 to 3, 35 to 50, and/or 95 to 105, wherein the amino acid residue numbering is based on the number shown in SEQ ID NO: 1.

In another preferred embodiment, the mutated amino acid residue site in the PDL-1 molecule is one or more amino acid residues in position 1, 36-40, 47-48, and/or 95-101, wherein the amino acid residue numbering is based on the number shown in SEQ ID NO: 1.

In another preferred embodiment, the number of mutated amino acid residue sites is n, wherein 1≤n≤15; preferably, 3≤n≤11; more preferably, 4≤n≤10, such as n can be 5, 6, 7, 8, 9, 10. In another preferred embodiment, the mutated amino acid residue site in the PDL-1 molecule includes one or more mutations of 1F, 36I, 38Y, 40E, 47I, 48Q, 95R, 97M, 99S, 101G, or an addition of one or more amino acids after 102G, wherein the amino acid residue numbering is based on the number shown in SEQ ID NO: 1.

In another preferred embodiment, the mutated amino acid residue sites in the PDL-1 molecule include 36I, 38Y, and 40E, wherein the amino acid residue numbering is based on the number shown in SEQ ID NO: 1.

In another preferred embodiment, the mutated amino acid residue sites in the PDL-1 molecule include 40E, and 47I, wherein the amino acid residue numbering is based on the number shown in SEQ ID NO: 1.

In another preferred embodiment, the mutated amino acid residue sites in the PDL-1 molecule include 95R, and 97M, wherein the amino acid residue numbering is based on the number shown in SEQ ID NO: 1.

In another preferred embodiment, the mutated PDL-1 molecule includes one or more amino acid residues selected from the group consisting of: 1W; 36Q, 36E, 36T, or 36N; 38F, 38N, 38H, or 38A; 40M, 40F, 40L, 40W or 40Y; 47L, 47V, 47F, 47S, 47Y, 47P or 47A; 48S; 95T, 95V or 95L; 97L; 99G or 99A; 101D, 101K, 101E or 101H; amino acid G inserted after 102G; wherein the amino acid residue numbering is based on the number shown in SEQ ID NO: 1.

In another preferred embodiment, the PDL-1 molecule includes: 36Q, 38H, and 40F; or
36E, 38H, and 40F; or
36Q, 38F, and 40M; or
36Q, 38F, and 40M, wherein the amino acid residue numbering is based on the number shown in SEQ ID NO: 1.

In another preferred embodiment, the PDL-1 molecule further includes: 48S, wherein the amino acid residue numbering is based on the number shown in SEQ ID NO: 1.

In another preferred embodiment, the PDL-1 molecule further includes: 47V, and 48S; or 47F, and 48S, wherein the amino acid residue numbering is based on the number shown in SEQ ID NO: 1.

In another preferred embodiment, the PDL-1 molecule further includes: 97L, wherein the amino acid residue numbering is based on the number shown in SEQ ID NO: 1.

In another preferred embodiment, the PDL-1 molecule further includes: 95T, 97L, 99G and 101K; or 95V, 97L, 99A, and 101K, wherein the amino acid residue numbering is based on the number shown in SEQ ID NO: 1.

In another preferred embodiment, the amino acid sequence of the PDL-1 molecule is selected from one of SEQ ID NOs: 5-34.

In another preferred embodiment, the PDL-1 molecule is soluble.

In another preferred embodiment, the C or N-terminus of the PDL-1 molecule has a conjugate.

In another preferred embodiment, the conjugate bound to the PDL-1 molecule is a T cell receptor, preferably, the T cell receptor is a high affinity T cell receptor.

In the second aspect of the present invention, a fusion protein is provided, wherein the fusion protein includes the PDL-1 molecule of the first aspect of the present invention.

In another preferred embodiment, the fusion protein further includes hIgG4Fc.

In the third aspect of the present invention, a multivalent PDL-1 complex is provided, wherein the multivalent PDL-1 complex comprises at least two PDL-1 molecules, and at least one of the PDL-1 molecules is the PDL-1 molecule as described in the first aspect of the present invention; or the multivalent PDL-1 complex comprises at least one fusion protein of the second aspect of the present invention.

In the fourth aspect of the present invention, a nucleic acid molecule is provided, wherein the nucleic acid molecule comprises a nucleic acid sequence, or a complementary sequence thereof encoding a PDL-1 molecule of the first aspect of the invention, a fusion protein of the second aspect of the invention, or a multivalent PDL-1 complex of the third aspect of the invention.

In the fifth aspect of the present invention, a vector is provided, wherein the vector includes the nucleic acid molecule of the fourth aspect of the present invention.

In the sixth aspect of the present invention, a host cell is provided, wherein the host cell contains the vector according to the fifth aspect of the present invention or the exogenous nucleic acid molecule according to the fourth aspect of the present invention is integrated within chromosome.

In the seventh aspect of the present invention, a pharmaceutical composition is provided, wherein the composition contains a pharmaceutically acceptable carrier and the PDL-1 molecule according to the first aspect of the present invention, or the fusion protein according to the second aspect of the present invention, or the PDL-1 complex according to the third aspect of the present invention.

In another preferred embodiment, the pharmaceutical composition further includes ImmTAC and/or HATac.

In the eighth aspect of the present invention, a method of treating disease is provided, which includes administering a suitable amount of a PDL-1 molecule according to the first aspect of the present invention, a fusion protein according to the second aspect of the present invention, or a PDL-1 complex according to the third aspect of the present invention, or a pharmaceutical composition according to the seventh aspect of the present invention to a subject in need of treatment.

In another preferred embodiment, the disease is the tumor.

In the ninth aspect of the present invention, a use of a PDL-1 molecule according to the first aspect of the present invention, a fusion protein according to the second aspect of the present invention, or a PDL-1 complex according to the third aspect of the present invention is provided, for preparing drugs for the treatment of tumors.

In the tenth aspect of the present invention, a method for preparing a PDL-1 according to the first aspect of the present invention is provided, including steps of:

(i) cultivating a host cell according to the sixth aspect of the present invention, thereby expressing the PDL-1 molecule according to the first aspect of the invention;

(ii) isolating or purifying the PDL-1 molecule.

It should be understood that in the present invention, any of the technical features specifically described above and below (such as in the Examples) can be combined with each other, thereby constituting new or preferred technical solutions that are not described one by one in the specification.

DESCRIPTION OF DRAWINGS

FIGS. 1A and 1B show the extracellular amino acid sequences and nucleotide sequences of wild-type PDL-1 molecules, respectively.

FIG. 2 shows the SDS-PAGE gel of purified wild-type PDL-1 protein.

FIGS. 3A and 3B show the amino acid sequences and nucleotide sequences of the refolded and purified PD-1 in example 2 of the present invention, respectively.

FIG. 4 shows a BIAcore map of binding of wild-type PDL-1 molecules to PD-1 molecules.

FIG. 5 shows the amino acid sequence of the high-affinity PDL-1 molecule of the present invention. Mutated or inserted amino acid residues are underlined.

FIGS. 6A and 6B show the α and β chain amino acid sequences of ImmTAC (1G4), respectively.

FIG. 7 shows the high-affinity PDL-1 molecule of the present invention significantly increases ImmTAC (1G4)-mediated killing of tumor cells by PBMC.

FIG. 8A shows an amino acid sequence of the hIgG4Fc molecule.

FIG. 8B shows an nucleotide sequence of the hIgG4Fc molecule.

DETAILED DESCRIPTION

Figure 9:
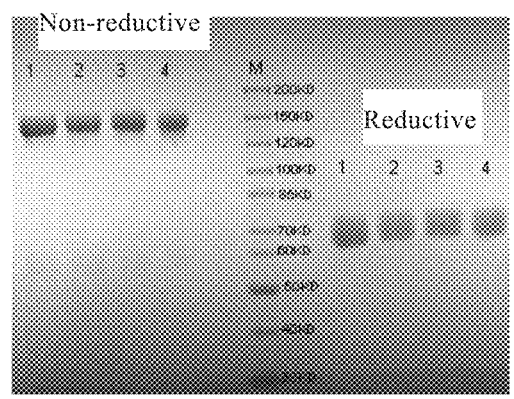
FIG. 9 shows a SDS-PAGE gel after purification of the wild-type PDL1-hIgG4Fc fusion protein.

Through extensive and intensive studies, the present inventors unexpectedly discovered that soluble PDL-1 molecules having high affinity for PD-1 molecules can effectively increase the killing ability of lymphocytes. Thus, the present invention provides a soluble high-affinity PDL-1 molecule, which has an affinity for PD-1 that is at least twice the affinity of the wild-type PDL-1 molecule for PD-1.

Specifically, the PDL-1 molecule in the present invention contains a mutation in the amino acid sequence as shown in SEQ ID NO: 1. More specifically, the amino acid sequence of the PDL-1 molecule has at least 90% sequence identity with the amino acid sequence as shown in SEQ ID NO: 1.

Before describing the present invention, it should be understood that the present invention is not limited to the specific methods and experimental conditions as the methods and conditions can be varied. It should also be understood that the terms used herein are for the purpose of describing a specific embodiment only, and are not intended to be limiting. The scope of the invention will only be limited by the appended claims.

Unless otherwise defined, all technical and scientific terms used herein have the same meaning as commonly understood by one of ordinary skill in the art to which this invention belongs.

Although any methods and materials similar or equivalent to those described herein can be used in the embodiment or test of the present invention, the preferred methods and materials are exemplified herein.

TERM

Wild-type PDL-1 molecule: The wild-type PDL-1 molecule according to the present invention refers to the extracellular region of the wild-type PDL-1 molecule, the amino acid sequence and nucleotide sequence thereof are shown in FIGS. 1A and 1B, respectively.

PBMC:

Peripheral blood mononuclear cells (PBMCs) are blood cells with rounded nuclei such as lymphocytes or monocytes. These blood cells are a key component of the immune system that resists infection and adapts to intruders. The lymphocyte population consists of T cells (about 75% of CD4 and CD8 positive), as well as B cells and NK cells (totally about 25%).

High affinity T cell receptor: referring to a T cell receptor, whose affinity of a ligand thereof is at least twice that of the corresponding wild type T cell receptor and a ligand thereof.

Tumor: referring to the growth or carcinogenesis for all types of cancer cells, metastatic tissue or malignant transformed cells, tissues or organs, regardless of pathological type or stage of infection. Examples of tumors include, but are not limited to: solid tumors, soft tissue tumors, and metastatic lesions. Examples of solid tumors include: malignant tumors of different organ systems, such as sarcoma, lung squamous cell carcinoma, and cancer. Fox example: infected prostate, lung, breast, lymph, intestines and stomach (e.g. colon), and genitourinary tract (e.g. kidney, epithelial cell), pharynx. Lung squamous cell carcinoma includes malignant tumors, for example, most colon cancer, rectal cancer, renal cell carcinoma, liver cancer, non-small cell lung cancer, small intestine cancer, and esophageal cancer. Metastatic lesions of the above cancer can also be treated and prevented with the methods and compositions of the present invention.

Pharmaceutical carriers: Also known as excipients or stabilizers. The dose and concentration used are non-toxic to the exposed cells or individuals thereof. Commonly, the physiologically acceptable carrier is a pH buffered aqueous solution. Examples of physiologically acceptable carriers include buffers such as phosphates, citrates and other organic acids; antioxidants, including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other saccharides, including glucose, mannose, or dextrins; chelating agents such as EDTA; sugar alcohols such as mannitol or sorbitol; salt forming counter ions such as sodium; and/or nonionic surfactants such as TWEEN™, polyethylene glycol (PEG) and PLURONICS™.

DETAILED DESCRIPTION OF THE INVENTION

PD-1 is an immuno-inhibitory receptor expressed on activated T cells and B cells. PDL-1 is a ligand for PD-1 and belongs to the B7 family. PDL-1 has IgV and IgC sample regions, tails of transmembrane domains and cytoplasmic domains. PDL-1 interacts with receptor PD-1 on lymphocytes and plays an important role in the negative regulation of immune responses. Through extensive and intensive studies, the present inventors unexpectedly discovered that soluble PDL-1 molecules having high affinity for PD-1 molecules can effectively increase the killing ability of lymphocytes. Thus, the present invention provides a soluble high-affinity PDL-1 molecule, which has an affinity for PD-1 that is at least twice the affinity of the wild-type PDL-1 molecule for PD-1.

The binding affinity (in inverse proportion to the dissociation equilibrium constant $K_D$) and the binding half-life (indicated as $T_{1/2}$) of the PDL-1 molecules to PD-1 as described above can be determined by any suitable method. It should be understood that doubling the affinity will result in a halving of $K_D$. $T_{1/2}$ is calculated as In2 divided by the dissociation rate ($K_{off}$). Therefore, doubling $K_{off}$ will result in a halving of $T_{1/2}$. The same test protocol is preferably used to detect the binding affinity or the binding half-life several times, for example 3 or more, and take the average of the results. In a preferred embodiment, these detections are performed using the Surface Plasmon Resonance (BIAcore) method in the embodiments of the present invention.

The method detects that the dissociation equilibrium constant $K_D$ of the wild-type PDL-1 molecule to PD-1 molecule in the present invention is 2.462E-05M, and the BIAcore binding pattern thereof is shown in FIG. 4. Since the doubling of affinity will lead to a halving of $K_D$, if the high-affinity PDL-1 molecule has a dissociation equilibrium constant $K_D$ of 1.231 E-05M for the PD-1 molecule, suggesting that the affinity of this high-affinity PDL-1 molecule to the PD-1 molecule is twice the affinity of the wild-type PDL-1 molecule to PD-1. The conversion relationship between $K_D$ value units is well-known for those skilled in the art that, that is, 1M=1000 μM, 1 μM=1000 nM, 1 nM=1000 pM.

In a preferred embodiment of the present invention, using the preferred method for measuring affinity of the present invention, the affinity of the PDL-1 molecule of the present invention to the PD-1 molecule is determined to be at least twice the affinity of the wild-type PDL-1 molecule to the PD-1 molecule; preferably, at least 5 times; more preferably, at least 10 times; most preferably, at least 50 times.

In another preferred embodiment, the affinity of the PDL-1 molecule to the PD-1 molecule is at least 100 times the affinity of the wild-type PDL-1 molecule to the PD-1 molecule; preferably, at least 200 times; more preferably, at least 500 times.

Specifically, the affinity $K_D$ of the high-affinity PDL-1 molecule to PD-1 of the present invention is ≤1.231E-05M; preferably 1.0E-06M≤$K_D$≤1.0 E-05M; more preferably 1.0E-07M≤$K_D$≤1.0 E-06M; most preferably 1.0E-08M≤$K_D$≤1.0 E-07M.

The high affinity PDL-1 molecule of the present invention contains one or more mutations in the amino acid sequence as shown in SEQ ID NO: 1. Specifically, the amino acid sequence of the PDL-1 molecule has at least 90% (preferably, at least 92%; more preferably, at least 94%, such as 95%, 96%, 97%, 98%, 99%) sequence identity with the amino acid sequence as shown in SEQ ID NO: 1.

More specifically, the mutated amino acid residue site in the high affinity PDL-1 molecule of the present invention includes one or more of 1F, 36I, 38Y, 40E, 47I, 48Q, 95R, 97M, 99S, 101G or one or more amino acids inserted after 102G, wherein the amino acid residue numbering is based on the number as shown in SEQ ID NO: 1.

In another preferred embodiment, the mutated PDL-1 molecule includes one or more amino acid residues selected from the group consisting of: 1W; 36Q, 36E, 36T, or 36N; 38F, 38N, 38H, or 38A; 40M, 40F, 40L, 40W or 40Y; 47L, 47V, 47F, 47S, 47Y, 47P or 47A; 48S; 95T, 95V or 95L; 97L; 99G or 99A; 101D, 101K, 101E or 101H; amino acid G inserted after 102G; wherein the amino acid residue numbering is based on the number as shown in SEQ ID NO: 1.

In another preferred embodiment, the amino acid sequence of the PDL-1 molecule is selected from one of SEQ ID NO: 5-34.

The wild-type PDL-1 molecules used in the present invention do not contain a transmembrane domain to obtain soluble and high-affinity PDL-1 molecules. Therefore, in a preferred embodiment of the present invention, the PDL-1 molecule is soluble.

Mutations can be performed using any suitable method, including but not limited to those based on polymerase chain reaction (PCR), restriction enzyme-based cloning, or ligation-independent cloning (LIC) methods. These methods are described in many standard molecular biology textbooks. For further details on polymerase chain reaction (PCR) mutagenesis and restriction enzyme-based cloning, see Sambrook and Russell, (2001) Molecular Cloning-A Laboratory Manual (third edition) CSHL Press. More information on the LIC method can be found in (Rashtchian, (1995) Curr Opin Biotechnol 6(1): 30-6).

The method for producing the high-affinity PDL-1 molecules of the present invention may be, but is not limited to, PDL-1 with high affinity for PD-1 was screened from a diversity library for displaying the phage particles of the PDL-1 molecules, as described in the literature (Li, et al (2005) Nature Biotech 23(3): 349-354).

It is understood that the gene expressing the wild-type PDL-1 of the present invention or the gene expressing the slightly modified wild-type PDL-1 of the present invention can be used to prepare the template strand. The required changes to produce the high affinity PDL-1 of the invention are then introduced into the DNA encoding the template strand.

The PDL-1 molecules of the invention can also be provided in the form of multivalent complexes. The multivalent PDL-1 of the present invention comprises two, three, four or more PDL-1 molecules of the present invention combined to form a polymer. A dimer can be prepared with an IgG FC fragment, as described in Example 5 of the present invention, or a tetramer can be produced by the tetrameric domain of p53, or multiple complexes formed by PDL-1 of the present invention in combination with another molecule.

The high-affinity PDL-1 molecules of the present invention may be used alone or may be covalently or otherwise combined with the conjugate, preferably covalently. The conjugate is preferably a T cell receptor, and more preferably, the T cell receptor is a high affinity T cell receptor.

The high affinity PDL-1 molecules of the present invention can also be used in combination with other molecules to produce an effective synergism. Preferably, the other molecule is ImmTAC or HATac. Both molecules are able to retarget T cells, thereby killing the target cells. The ImmTAC molecule is a fusion molecule of a soluble double-stranded TCR molecule containing an artificial inter-chain disulfide bond and an anti-CD3 antibody between constant regions of α β, see the literature (Joanne Oates, Bent K. Jakobsen. (ImmTACs) Novel bi-specific agents for targeted cancer therapy. OncoImmunology 2:2, e22891, February 2013). The HATac molecule is a high-affinity T-cell activation core, wherein one form is a fusion molecule of a soluble single-chain TCR molecule and an anti-CD3 antibody linked by the variable domains of α and β chains mutated from a hydrophobic core. The soluble single-chain TCR molecules can be specifically referred to patent document WO2014/206304.

The invention also relates to a nucleic acid molecule encoding PDL-1 of the invention. The nucleic acid molecules of the invention can be in form of DNA or RNA. DNA can be a coding or non-coding strand. For example, a nucleic acid sequence encoding a TCR of the present invention can be the same as or a degenerate variant of the nucleic acid sequence shown in the drawings of the present invention. Illustrating the meaning of "degenerate variant", as used herein, "degenerate variant" refers to a nucleic acid sequence encoding a protein sequence of SEQ ID NO: 1 but differs from the sequence of SEQ ID NO: 2 in the present invention.

The full-length nucleic acid molecule sequence or a fragment thereof of the present invention can usually be obtained by methods, but not limited to PCR amplification, recombination or artificial synthesis. At present, DNA sequences encoding PDL-1 (or a fragment thereof, or a derivative thereof) of the present invention can be obtained completely by chemical synthesis. The DNA sequence can then be introduced into various existing DNA molecules (or vectors) and cells known in the art.

The invention also relates to a vector comprising a nucleic acid molecule of the invention, and a host cell produced by genetic engineering using the vector or coding sequence of the present invention.

The invention also provides a pharmaceutical composition, the pharmaceutical composition contains a pharmaceutically acceptable carrier and the PDL-1 of the present invention, or the PDL-1 complex of the present invention.

The present invention also provides a method for treating diseases, comprising administering an appropriate amount of the PDL-1 of the present invention, or the PDL-1 complex of the present invention, or the pharmaceutical composition of the present invention to a subject in need of treatment; in particular, the PDL-1 molecule of the present invention is used in combination with other molecules, preferably, the other molecule is ImmTAC or HATac.

It should be understood that the amino acid names herein are identified by the international single English letters, and the corresponding amino acid names are abbreviated as: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), Val (V); in the art, the function of the protein will not be changed when the amino acids are substituted with those having similar or similar properties. The structure and function of the protein will not also be changed when addition of one or several amino acids at the C-terminus and/or N-terminus.

The present invention also includes slightly modified PDL-1 molecules for PDL-1 of the present invention. Modifications (usually without changing primary structure) include: chemically derivatized form of PDL-1 of the present invention such as acetylation or carboxylation. Modifications also include glycosylation, such as those PDL-1 molecules produced by glycosylation modifications in the synthesis and processing of the PDL-1 of the present invention or in further processing steps. This modification can be accomplished by exposing PDL-1 to enzymes that undergo glycosylation (e.g. mammalian glycosylase or deglycosylation enzyme). Modified forms also include sequences with phosphorylated amino acid residues (e.g., phosphotyrosine, phosphoserine, phosphothreonine), and also include PDL-1 that has been modified to increase its resistance to proteolysis or to optimize solubility.

The PDL-1 or PDL-1 complex of the invention can be provided in a pharmaceutical composition together with a pharmaceutically acceptable carrier. The PDL-1, multivalent PDL-1 complex of the invention is generally provided as part of a sterile pharmaceutical composition, the composition typically includes a pharmaceutically acceptable carrier. The pharmaceutical composition can be in any suitable form (depending on the desired method of administration to the patient). It can be provided in unit dosage form, usually in a sealed container, and may be provided as part of a kit. Such kits (but not necessarily) include instructions for use. It can include a plurality of said unit dosage forms. In addition, the PDL-1 of the present invention can be used alone or in combination or coupled with other therapeutic agents (eg, formulated in the same pharmaceutical composition).

The pharmaceutical composition can also contain a pharmaceutically acceptable carrier. The term "pharmaceutically acceptable carrier" refers to a carrier for the administration of a therapeutic agent. The term refers to pharmaceutical carriers that do not induce the generation of antibodies that are harmful to the individual receiving the composition, and are not excessive toxicity after administration. These vectors are well-known to those of ordinary skill in the art. A full discussion of pharmaceutically acceptable excipients can be found in Remington's Pharmaceutical Sciences (Mack Pub. Co., N.J. 1991). Such carriers include, but are not limited to, saline, buffer, dextrose, water, glycerol, ethanol, adjuvants, and combinations thereof.

Pharmaceutically acceptable carriers in therapeutic compositions can contain liquids such as water, saline, glycerol, and ethanol. In addition, auxiliary substances may also be present in these carriers, such as wetting agents or emulsifiers, pH buffer substances, etc. In general, the therapeutic compositions can be prepared as injections, for example liquid solutions or suspensions; solid forms suitable for formulation in a solution or in a suspension, in a liquid vehicle prior to injection can also be prepared. Once formulated into a composition of the invention, it can be administered by conventional routes including, but not limited to: intraocular, intramuscular, intravenous, subcutaneous, intradermal, or topical administration, preferably parenteral, including subcutaneous, intramuscular, or intravenous. The subject to be prevented or treated can be an animal; especially human.

When the pharmaceutical composition of the present invention is used in actual treatment, various different dosage forms of the pharmaceutical composition can be used depending on the usage. Preferred examples include injections, oral preparation, and the like. These pharmaceutical compositions can be formulated by mixing, diluting, or dissolving according to conventional methods, and occasionally adding suitable pharmaceutical additives such as excipients, disintegrants, binders, lubricants, diluents, buffers, isotonicities, preservatives, wetting agents, emulsifiers, dispersants, stabilizers, and co-solvents, and the formulation process can be performed according to the dosage form in the usual manner.

The pharmaceutical composition of the present invention can also be administered as a sustained release agent. For example, the PDL-1 of the present invention may be incorporated into a pellet or microcapsule with a sustained release polymer as a carrier, and then the pellet or microcapsule may be surgically implanted into the tissue to be treated. As examples of the sustained-release polymer, ethylene-vinyl acetate copolymers, polyhydrometaacrylates, polyacrylamides, polyvinylpyrrolidone, methylcellulose, lactic acid polymers, lactic acid-glycolic acid copolymers, and the like may be exemplified. Preferred are biodegradable polymers such as lactic acid polymers and lactic acid-glycolic acid copolymers.

When the pharmaceutical composition of the present invention is used in actual treatment, the PDL-1 or PDL-1 complex of the present invention as an active ingredient can be reasonably determined according to the weight, age, sex, degree of symptoms of each patient to be treated, and the proper amount is finally determined by physician.

Main Advantages of the Present Invention are:
(1) The present invention obtains PDL-1 molecules with high affinity for PD-1.
(2) The high-affinity PDL-1 molecule of the present invention can effectively increase the killing ability of lymphocytes.

The present invention will be further illustrated below with references to the specific examples. It should be understood that these examples are only to illustrate the invention but not to limit the scope of the invention. The experimental methods with no specific conditions described in the following examples are generally performed under the conventional conditions, such as Sambrook and Russell et al., Molecular Cloning-A Laboratory Manual (Third Edition) (2001) CSHL Press, or according to the manufacture's instructions. Unless indicated otherwise, parts and percentage are calculated by weight. The experimental materials and reagents used in the following examples were obtained from commercial sources unless otherwise specified.

Example 1: Expression, Refolding, and Purification of Wild-Type PDL-1

The extracellular amino acid sequence and nucleotide sequence of the wild-type PDL-1 are SEQ ID NOs: 1 and 2, respectively. As shown in FIGS. 1A and 1B, the gene of interest carrying the extracellular sequence of wild-type PDL-1 was double-digested with NcoI and NotI and ligated with the pET28a vector digested with NcoI and NotI. The ligation product was transformed into *E. coli* DH5α, coated with LB plate containing kanamycin, inverted cultured at 37° C. overnight, positive clones were picked for PCR screening, the positive recombinants were sequenced, and the correct sequence was determined, and the recombinant plasmid was extracted and transformed to *E. coli* BL21 (DE3) for expression.

The above mentioned BL21 (DE3) colonies containing the recombinant plasmid pET28a-PDL-1 were all inoculated into a LB medium containing kanamycin, cultured at 37° C. until the OD600 was 0.6-0.8, and IPTG was added to a final concentration of 0.5 mM. The culture was continued for 4 h at 37° C. Cell pellets were harvested by centrifugation at 5000 rpm for 15 min, cell pellets were lysed with Bugbuster Master Mix (Merck), centrifuged at 6000 rpm for 15 min to recover inclusion bodies, washed with Bugbuster (Merck) to remove cell debris and membrane fractions, and centrifuged at 6000 rpm for 15 min. Inclusion bodies were collected. The inclusion bodies were dissolved in a buffer (50 mM Tris-HCl, 200 mM NaCl, 2 mM EDTA, 6 M guanidine HCl, pH 8.0), and the insoluble substances were removed by high-speed centrifugation. The supernatant was quantified by BCA and then dispensed and stored at −80° C. until use.

2 mL of buffer (50 mM Tris-HCl, 200 mM NaCl, 2 mM EDTA, 6 M guanidine HCl, pH 8.0) was added to 7 mg of soluble PDL-1 inclusion body protein, DTT was added to a final concentration of 10 mM, and the solution was treated at 37° C. for 30 min. The treated PDL-1 was added dropwise to a 100 mL renaturation buffer (50 mM HEPES, pH 7.5, 500 mM L-arginine, 9 mM glutathione, 1 mM glutathione disulfide, 24 mM NaCl, 1 mM KCl) using a syringe. After stirring at 4° C. for 30 min, the renaturation solution was loaded into a cellulose membrane dialysis bag with a 3.5 kDa of cut-off. The dialysis bag was placed in 2 L of pre-cooled water and slowly stirred overnight at 4° C. After 24 hours, the dialysate was changed to 2L of pre-cooled buffer (10 mMTris-HCl pH 8.0), and dialysis was continued for 24 h at 4° C. The dialysate was then replaced with the same fresh buffer and dialysis was continued for 24 hours. The sample was filtered through a 0.45 um filter, vacuum degassed and passed through an anion exchange column (HiTrap Q HP, GE Healthcare), the protein was purified with 0-1M NaCl linear gradient elution formulated with 10 μM Tris-HCl pH 8.0. The eluted fractions collected were subjected to SDS-PAGE analysis, and the SDS-PAGE gel was shown in FIG. 2. The PDL-1 fraction was concentrated and further purified on a gel filtration column (Superdex 75 10/300, GE Healthcare). The target fraction was also subjected to SDS-PAGE analysis.

The eluted fractions used for BIAcore analysis were further tested for purity thereof using gel filtration. The conditions were: column Agilent Bio SEC-3 (300 A, φ7.8× 300 mm), mobile phase: 150 mM phosphate buffer, flow rate: 0.5 mL/min, column temperature: 25° C., UV detection wavelength: 214 nm.

Example 2: Characterization for Combination

BIAcore Analysis

The BIAcore T200 real-time analysis system was used to detect the binding activity of the wild-type PDL-1 molecule to PD-1. The anti-streptavidin antibody (GenScript) was added to the coupling buffer (10 mM sodium acetate buffer, pH 4.77). The antibody was then flowed through a CM5 chip previously activated with EDC and NHS to immobilize the antibody on the chip surface. Finally, the unreacted activation surface was blocked with a solution of ethanolamine hydrochloride to complete the coupling process. The coupling level is approximately 15,000 RU.

A low concentration of streptavidin is allowed to flow over the surface of the antibody-coated chip, then the biotinylated PD-1 is passed through the detection channel and the other channel is used as a reference channel. Then, 0.05 mM biotin was passed through the chip at a flow rate of 10 μL/min for 2 min to block the remaining binding sites of streptavidin. The single-cycle kinetic analysis method was used to measure its affinity. PDL-1 was diluted with HEPES-EP buffer (10 mM HEPES, 150 mM NaCl, 3 mM EDTA, 0.005% P20, pH 7.4) to several different concentrations and successively flowed through the chip surface at a flow rate of 30 μL/min. The binding time for each injection was 120 s, and it was disassociated for 600 s after the last injection. The chips were regenerated with 10 mMGly-HCl, pH 1.75 after each round of assays. Kinetic parameters were calculated using BIAcore Evaluation software.

The amino acid sequence and nucleotide sequence of PD-1 used in this example are shown in FIGS. 3A and 3B, respectively. The expression, renaturation and purification processes are the same as those of the wild-type PDL-1 in Example 1. Biotinylation process thereof is as follows:

a. Biotinylation

The purified PD-1 molecule was concentrated using a Millipore ultrafiltration tube while the buffer was replaced with 10 mMTris pH 8.0, then biotinylation reagents of 0.05 M Bicine pH 8.3, 10 mM ATP, 10 mM MgOAc, 50 μM D-Biotin, 100 μg/ml BirA enzyme (GST-BirA) were added. The mixture was incubated at room temperature overnight and SDS-PAGE was used to determine if biotinylation was complete.

b. Purification of Biotinylated Complexes

The biotinylated PD-1 molecule was concentrated to 1 ml using a Millipore ultrafiltration tube, and the biotinylated PD-1 was purified by gel filtration chromatography. 1 ml of the concentrated biotinylated PD-1 molecule was loaded with a filtered PBS pre-equilibrated HiPrep™ 16/60 5200 HR column (GE General Electric) and then eluted with PBS at a flow rate of 1 ml/min using an Akta purifier (GE General Electric). The biotinylated PD-1 molecule eluted as a single peak at about 10 ml. The protein-containing fractions were pooled, concentrated using a Millipore ultrafilter, the BCA method (Thermo) was used to determine the protein concentration, and the biotinylated PD-1 fraction was stored at −80° C.

The $K_D$ value of the binding affinity of the wild-type PDL-1 molecule to the PD-1 molecule detected by the above procedure of the present example was 2.462E-05M, and the BIAcore binding pattern thereof is shown in FIG. 4.

Example 3: Generation of High Affinity PDL-1 Molecules

The extracellular sequence of wild-type PDL-1 described in Example 1 was used as a template strand. Screening of high affinity PDL-1 was performed according to the phage display and screening methods described by Li et al. ((2005) Nature Biotech 23(3):349-354). After several rounds of screening, the phage libraries had strong binding signals with PD-1, and single clone was picked from the phage library for sequence analysis.

Expression, renaturation and purification of the high affinity PDL-1 molecules of the present invention are performed as described in Example 1, and the affinity with the PD-1 molecule was determined as described in Example 2. The affinity of the high-affinity PDL-1 molecule obtained in the present invention to the PD-1 molecule is at least twice that of the wild-type PDL-1 molecule to the PD-1 molecule.

The amino acid sequence thereof is shown in FIG. 5, and the affinity values thereof with the PD-1 molecule are shown in Table 1 below.

TABLE 1

| NO. of High affinity PDL-1 molecule | SEQ ID NO | $K_{on}$ (1/Ms) | $K_{off}$ (1/s) | $K_D$ (M) |
|---|---|---|---|---|
| L1C2 | 5 | 5.010E+04 | 3.762E−02 | 7.509E−07 |
| L1F2 | 6 | 3.017E+04 | 1.039E−01 | 3.444E−06 |
| L1A4 | 7 | 4.797E+04 | 4.386E−02 | 9.143E−07 |
| L22A5 | 8 | 1.154E+04 | 5.588E−02 | 4.844E−06 |
| L2B6 | 9 | 1.299E+04 | 1.339E−01 | 1.031E−05 |
| L2F4 | 10 | 2.050E+04 | 1.545E−01 | 7.538E−06 |
| L2F5 | 11 | 1.216E+04 | 1.224E−01 | 1.006E−05 |
| L2D7 | 12 | 1.134E+04 | 1.234E−01 | 1.088E−05 |
| L2H3 | 13 | 1.710E+04 | 1.534E−01 | 8.969E−06 |
| L2G10 | 14 | 3.874E+04 | 1.783E−01 | 4.603E−06 |
| L2C4 | 15 | 1.102E+04 | 1.236E−01 | 1.122E−05 |
| L22C7 | 16 | 1.116E+04 | 1.326E−01 | 1.188E−05 |
| L2B8 | 17 | 1.281E+04 | 1.498E−01 | 1.170E−05 |
| L22D5 | 18 | 4.141E+04 | 2.681E−01 | 6.475E−06 |
| L2A6 | 19 | 9.669E+03 | 4.582E−02 | 4.739E−06 |
| L3B3 | 20 | 1.422E+05 | 7.099E−02 | 4.994E−07 |
| L3B3a | 21 | 1.616E+05 | 9.000E−02 | 5.570E−07 |
| L3B3b | 22 | 8.602E+04 | 5.729E−02 | 6.659E−07 |
| L3B3C | 23 | 6.781E+04 | 4.398E−02 | 6.485E−07 |
| L3B3d | 24 | 5.454E+04 | 5.258E−02 | 9.641E−07 |
| L3C7 | 25 | 4.387E+04 | 3.290E−02 | 7.500E−07 |
| L3C7a | 26 | 1.203E+05 | 1.386E−02 | 1.152E−07 |
| L3C7b | 27 | 1.433E+05 | 1.759E−02 | 1.227E−07 |
| L3C7c | 28 | 1.470E+05 | 1.555E−02 | 1.058E−07 |
| L3C7d | 29 | 1.094E+05 | 5.902E−03 | 5.393E−08 |
| L3D9 | 30 | 2.570E+04 | 8.714E−02 | 3.391E−06 |
| L32G5 | 31 | 5.664E+04 | 1.685E−01 | 2.975E−06 |
| L3G10 | 32 | 2.220E+04 | 2.628E−01 | 1.184E−05 |
| L32H8 | 33 | 4.342E+04 | 1.240E−02 | 2.856E−06 |
| L4D6 | 34 | 1.768E+04 | 2.011E−01 | 1.137E−05 |

Example 4: The Effect of High Affinity PDL-1 Molecule on the Killing Effect of PBMC (Peripheral Blood Mononuclear Cells) on Tumor Cell Line (A375)

This example uses a non-radioactive cytotoxicity test to verify the killing effect. This assay is a colorimetric alternative to the 51 Cr release cytotoxicity assay that quantitatively measures lactate dehydrogenase (LDH) released after cell lysis. A 30-minute coupled enzyme assay was used to detect the released LDH in the culture supernatant, which converted the tetrazolium salt (INT) into a red formazan product. The amount of color formed is proportional to the number of lysed cells. Absorbance data at 490 nm was collected using a standard 96 well plate reader.

The materials used were as follows: CytoTox96 non-radioactive cytotoxicity assay (Promega) (G1780) contains a substrate mix, assay buffer, lysis solution, and stop solution; Test medium: 10% FBS (heat-inactivated, Gibbco, Cat. number 10108-165), VIVO-15 (Lonza), Cat. number: 04-418); Nunc microwell round-bottomed 96-well tissue culture plates (Nunc, Cat. No. 163320); Nunc-immunized plate Maxisorb (Nickel, Cat. No. 442404).

The target cells used in this example were A375 cells (purchased from ATCC, Cat. No. CRL-1619). Target cells were prepared in test medium; the target cell concentration was adjusted to $2\times10^{\wedge}5$ cells/ml to obtain $2\times10^{\wedge}4$ cells/well, 100 μl.

The effector cells (PBMC cells) used in this example were sorted from fresh white tunica of healthy people. The cells were resuspended at $1\times10^6$ cells/ml in the test medium to obtain $1\times10^5$ cells/well, 100 μl.

The final concentration of ImmTAC in the experiment was $10^{\wedge}-9M$, and the storage concentration of ImmTAC was $13\times10^{-6}M$, which was diluted 13,000-fold and was directly added to the prepared effector cells. The final concentration of different high affinity PDL1 is 30 μg/ml. The α and β chain amino acid sequences of ImmTAC used in this example were shown in FIGS. 6A and 6B, respectively.

The components of the test were added to the plate using the following sequence: 100 μl of target cells (prepared as described above) were added to each well; 100 μl of effector cells (prepared as described above) were added to each well; different high affinity PDL1 was added to each well.

Several controls were prepared as follows: Spontaneous release of effector cells: only 200 μl of effector cells; Spontaneous release of target cells: only 200 μl of target cells; Maximum release of target cells: only 200 μl of target cells. All wells were prepared in triplicate and the final volume was 200 μl. Plates were centrifuged at 250×g for 4 minutes and then incubated at 37° C. for 24 hours. 20 μl of the lysis solution was added to the target cell maximal release control well and the supernatant was collected after 45 minutes. Plates were centrifuged at 250×g for 4 minutes. 50 μl of supernatant from each well of the assay plate was transferred to the corresponding well of a flat-bottomed 96 well Nunc Vlnxisorb plate. The substrate mixture was reconstituted with assay buffer (12 ml). Then 50 μl of the reconstituted substrate mixture was added to each well of the plate. The plate was covered with aluminum foil and incubated at room temperature for 30 minutes. 50 μl of stop solution was added to each well of the plate to stop the reaction. The absorbance at 490 nm was recorded on an Elisa plate reader within 1 hour after addition of the stop solution.

Calculation of results: The average absorbance of the background was deducted from absorbance values of the test, target cell spontaneous release, and average absorbance value of volume-calibrated control was deducted from absorbance value obtained from maximum release control of target cells. The calibration values obtained in the previous two steps were used in the following formula to calculate the percentage of cytotoxicity: % cytotoxicity=100×(test−target cell spontaneous−effector cell spontaneous)/(target cell maximum−target cell spontaneous).

The results of the experiment were shown in FIG. 7. PDL1 is a wild-type PDL-1 molecule in the histogram of the subscript "PBMC+A375+1G4+PDL1" in FIG. 7. The increase or decrease in the lysis rate in the figure was relative to the "PBMC+A375+1G4" histogram. The specific calculation was |("PBMC+A375+1G4+PDL-1 molecule")−"PBMC+A375+1 G4")|/"PBMC+A375+1 G4". This result showed that part of the high-affinity PDL-1 molecule of the present invention significantly increased the killing effect of PBMCs on tumor cells.

Example 5: Construction, Expression and Purification of High Affinity PDL1 Dimer Proteins Human immunoglobulin fragment crystallizable (h1gG4Fc) was used to construct dimers of high affinity PDL1 molecules. Specifically, the 3'-end of the high-affinity PDL-1 extracellular nucleotide sequence and the 5'-end of the hIgG4Fc nucleotide sequence were connected by overlap PCR to obtain the nucleic acid sequence and amino acid sequence of the fusion protein. The hIgG4Fc amino acid sequence and nucleic acid sequence were SEQ ID NOs: 37 and 38, respectively as shown in FIGS. 8A and 8B. The gene of interest carrying the fusion protein sequence was double digested with EcoRI and NotI, and ligated with EcoRI and NotI-digested pcDNA3.1(+) vector. The ligation product was transformed into TOP10, ampicillin-containing LB plates were coated and inverted cultured overnight at 37° C. Positive clones were picked for PCR screening and positive recombinants were sequenced. After the sequence was determined to be correct, the recombinant plasmid was extracted and transiently transferred to 293T cells for expression. The dimer of the wild-type PDL1 molecule is constructed in the same manner as described above, and the dimer of the wild-type PDL1 molecule is expressed in the present invention as PDL1-hIgG4. Dimers of high-affinity PDL1 molecules are expressed in the present invention as high-affinity PDL1 molecule numbering-hIgG4, such as L2D7-hIgG4.

$1 \times 10^7$ 293T cells (purchased from ATCC, Cat. No. CRL-11268) were inoculated into 10 cm cell culture dishes, washed with PBS once after 12 h, and replaced with opti-MEM medium. Lipo2000: Recombinant plasmid (1 μg/μl) was added to opti-MEM at a ratio of 2:1 and placed for 5 min at room temperature. The opti-MEM containing lipo2000 was added dropwise to the opti-MEM containing the recombinant plasmid, mixed and placed at room temperature for 20 min. 293T cells that had been replaced with opti-MEM medium were replaced with Freestyle™ 293 medium after 4 hours and cultured in a 5% $CO_2$ incubator at 37° C. for 3 days.

The culture supernatant was collected, filtered through a 0.45 um filter, and the protein was purified by an anion exchange column (HiTrap Q HP, GE Healthcare) using a linear gradient elution of 0-1 M NaCl in 20 mM Tris-HCl pH 7.0. Elution fractions collected were subjected to SDS-PAGE analysis. Take PDL1-hIgG4Fc as an example, the SDS-PAGE gel was shown in FIG. 9. The fractions were concentrated and further purified on a gel filtration column (Superdex 200 10/300, GE Healthcare). The target fractions were also subjected to SDS-PAGE analysis.

The materials used were as follows: 10 cm cell culture dish (greiner, Cat. Number: 627160), opti-MEM medium (gibco, Cat. Number: 31985-070), Lipo2000, Freestyle™ 293 medium (gibco, Cat. Number: 12338-018), PureLink™ HiPure Plasmid Maxiprep Kit (invitrogen, Cat. Number: K2100-06)

Example 6: The Effect of High Affinity PDL1-hIgG4Fc Fusion Protein on the Killing Effect of PBMC (Peripheral Blood Mononuclear Cells) on Tumor Cell Lines This example uses a non-radioactive cytotoxicity test to verify the killing effect. This assay is a colorimetric alternative to the 51 Cr release cytotoxicity assay that quantitatively measures lactate dehydrogenase (LDH) released after cell lysis. A 30-minute coupled enzyme assay was used to detect the released LDH in the culture supernatant, which converted the tetrazolium salt (INT) into a red formazan product. The amount of color formed is proportional to the number of lysed cells. Absorbance data at 490 nm was collected using a standard 96 well plate reader.

The materials used were as follows: CytoTox96 non-radioactive cytotoxicity assay (Promega) (G1780) contains a substrate mix, assay buffer, lysis solution, and stop solution; Test medium: 10% FBS (heat-inactivated, Gibbco, Cat. number 10108-165), VIVO-15 (Lonza), Cat. number: 04-418); Nunc microwell round-bottomed 96-well tissue culture plates (Nunc, Cat. No. 163320); Nunc-immunized plate Maxisorb (Nickel, Cat. No. 442404).

The target cells used in this example were Mel624 cells (available from Cassian Yee Lab), NCI-H1299 cells (purchased from ATCC, Cat. No. CRL-5803), IM9 cells (purchased from ATCC, Cat. No. CRL-159), MDA-MB-231 cells (purchased from ATCC, Cat. No. CRM-HTB-26). Target cells were prepared in test medium; the target cell concentration was adjusted to $2 \times 10^{\wedge}5$ cells/ml to obtain $2 \times 10^{\wedge}4$ cells/well, 100 μl.

The effector cells (PBMC cells) used in this example were sorted from fresh white tunica of healthy people. The cells were resuspended at $1 \times 10^{\wedge}6$ cells/ml in the test medium to obtain $1 \times 10^{\wedge}5$ cells/well, 100 μl.

The final concentration of ImmTAC in the experiment was $10^{\wedge}-9M$, and the storage concentration of ImmTAC was $5 \times 10^{\wedge}-6M$, which was diluted 5000-fold and was directly added to the prepared effector cells. The final concentration of different high affinity PDL1-hIgG4Fc fusion protein is 20 μg/ml. The α and β chain amino acid sequences of ImmTAC (1G4) used in this example were shown in FIGS. 6a and 6b, respectively.

The components of the test were added to the plate using the following sequence: 100 μl of target cells (prepared as described above) were added to each well; 100 μl of effector cells (prepared as described above) were added to each well; different high affinity PDL1-hIgG4Fc fusion protein was added to each well.

Several controls were prepared as follows: Spontaneous release of effector cells: only 200 μl of effector cells; Spontaneous release of target cells: only 200 μl of target cells; Maximum release of target cells: only 200 μl of target cells. All wells were prepared in triplicate and the final volume was 200 μl. Plates were centrifuged at 250×g for 4 minutes and then incubated at 37° C. for 20 hours. 20 μl of the lysis solution was added to the target cell maximal release control well and the supernatant was collected after 45 minutes. Plates were centrifuged at 250×g for 4 minutes. 50 μl of supernatant from each well of the assay plate was transferred to the corresponding well of a flat-bottomed 96 well Nunc Vlnxisorb plate. The substrate mixture was reconstituted with assay buffer (12 ml). Then 50 μl of the reconstituted substrate mixture was added to each well of the plate. The plate was covered with aluminum foil and incubated at room temperature for 30 minutes. 50 μl of stop solution was added to each well of the plate to stop the reaction. The absorbance at 490 nm was recorded on an Elisa plate reader within 1 hour after addition of the stop solution.

Calculation of results: The average absorbance of the background was deducted from absorbance values of the test, target cell spontaneous release, and average absorbance value of volume-calibrated control was deducted from absorbance value obtained from maximum release control of target cells. The calibration values obtained in the previous two steps were used in the following formula to calculate the percentage of cytotoxicity: % cytotoxicity=100×(test−target cell spontaneous−effector cell spontaneous)/(target cell maximum−target cell spontaneous).

The experimental results were shown in FIGS. 10A, 10B, 10C and 10D.

Figure 10A:
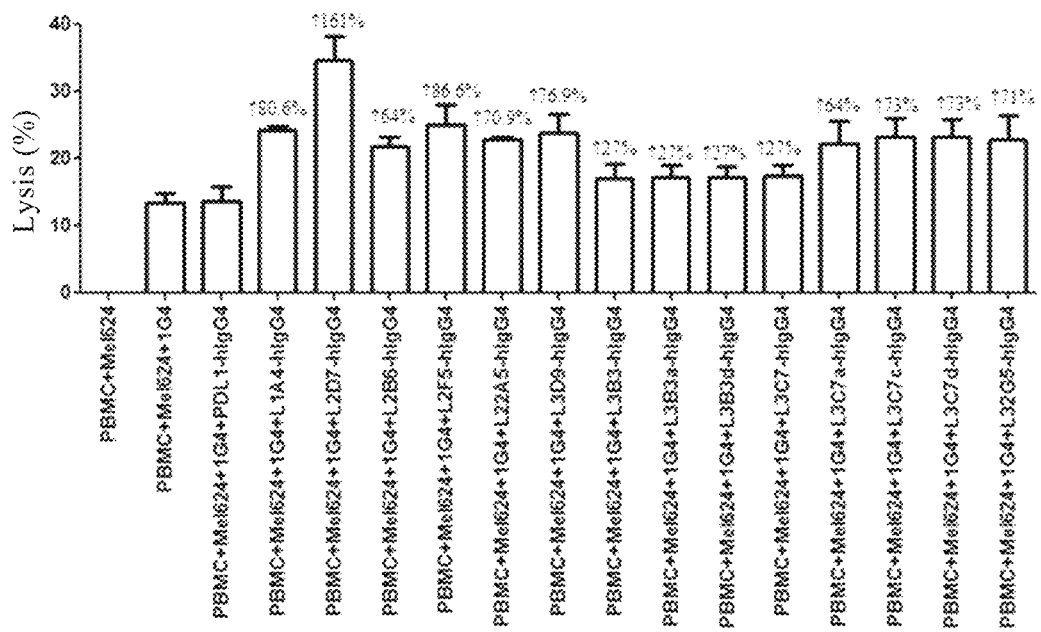
FIG. 10A shows the high-affinity PDL1-hIgG4Fc fusion protein of the present invention significantly increases ImmTAC (1G4)-mediated killing of tumor cell Mel624 by PBMC.

PDL1-h1gG4 in the histogram of "PBMC+Mel624+1G4+PDL1-h1gG4" in FIG. 10A was the wild-type PDL-1 fusion molecule. The increase or decrease in the lysis rate in the figure was relative to the "PBMC+Mel624+1G4" histogram. The specific calculation was |("PBMC+Mel624+1G4+high affinity PDL1-h1gG4 molecule"-"PBMC+Mel624+1G4+PDL1-h1gG4 molecule")|/"PBMC+Mel624+1G4+PDL1-h1gG4 molecule". This result showed that part of the high-affinity PDL-1 fusion molecule of the present invention significantly enhanced the killing effect of PBMC on tumor cell Mel624.

Figure 10B:
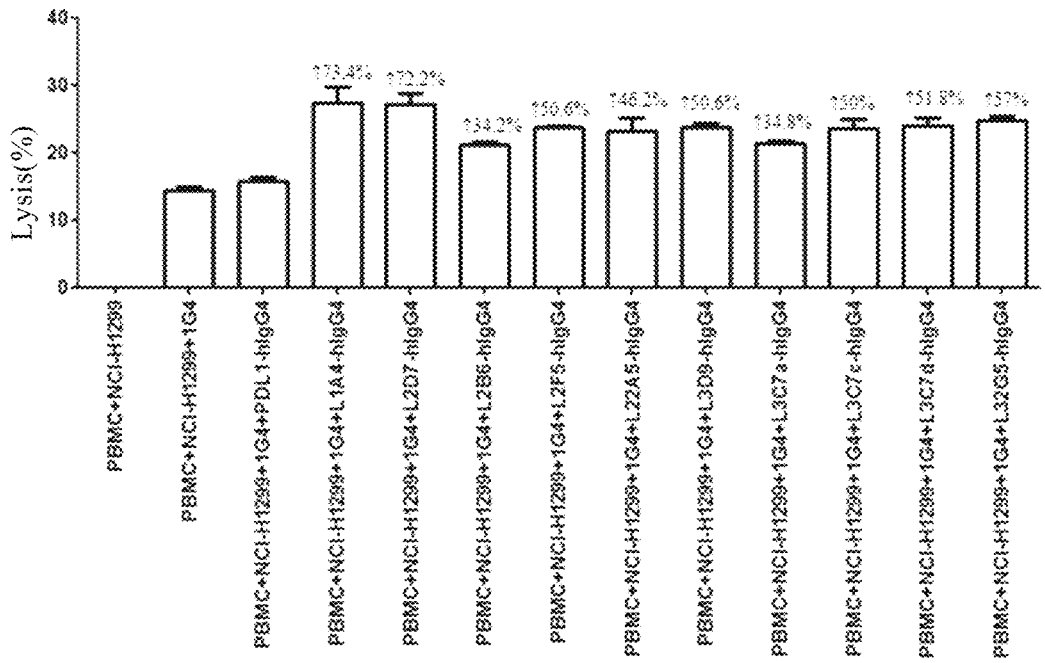
FIG. 10B shows the high-affinity PDL1-hIgG4Fc fusion protein of the present invention significantly increases ImmTAC (1G4)-mediated killing of tumor cell NCI-H1299 by PBMC.

PDL1-h1gG4 in the histogram of "PBMC+NCI-H1299+1G4+PDL1-h1gG4" in FIG. 10B was the wild-type PDL-1 fusion molecule. The increase or decrease in the lysis rate in the figure was relative to the "PBMC+NCI-H1299+1G4" histogram. The specific calculation was |("PBMC+NCI-H1299+1G4+high affinity PDL1-h1gG4 molecule"−"PBMC+NCI-H1299+1G4+PDL1-h1gG4 molecule")|/"PBMC+NCI-H1299+1G4+PDL1-h1gG4 molecule." This result showed that part of the high-affinity PDL-1 fusion molecule of the present invention significantly enhanced the killing effect of PBMC on tumor cell NCI-H1299.

Figure 10C:
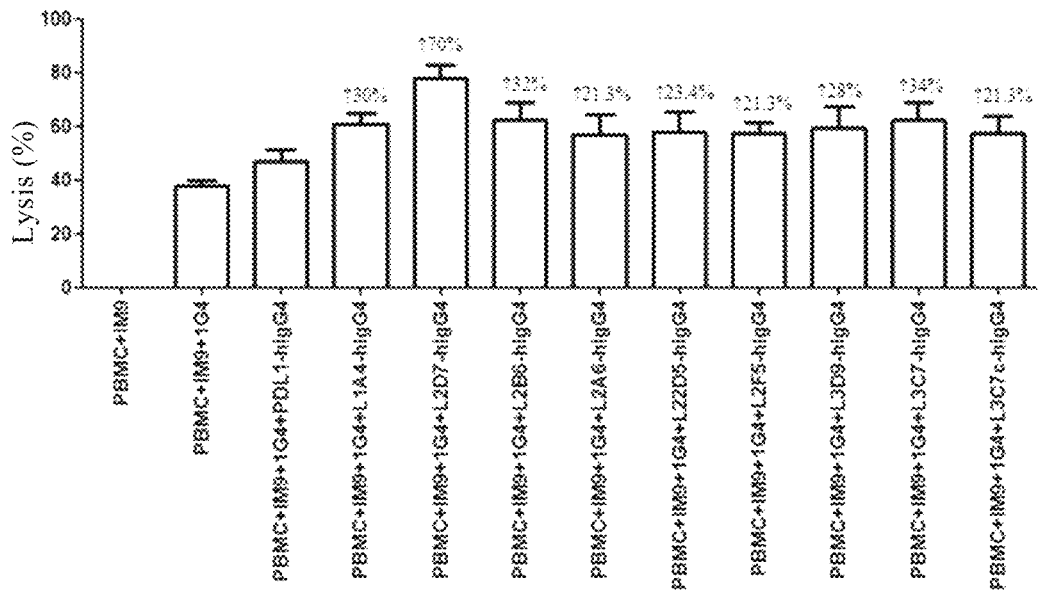
FIG. 10C shows the high-affinity PDL1-hIgG4Fc fusion protein of the present invention significantly increases ImmTAC (1G4)-mediated killing of tumor cell IM9 by PBMC.

PDL1-h1gG4 in the histogram of "PBMC+IM9+1G4+PDL1-h1gG4" in FIG. 10C was the wild-type PDL-1 fusion molecule. The increase or decrease in the lysis rate in the figure was relative to the "PBMC+IM9+1G4+PDL1-h1gG4" histogram. The specific calculation was |("PBMC+IM9+1G4+high affinity PDL1-h1gG4 molecule"−"PBMC+IM9+1G4+PDL1-h1gG4 molecule")|/"PBMC+IM9+1G4+PDL1-h1gG4 molecule". This result showed that part of the high-affinity PDL-1 fusion molecule of the present invention significantly enhanced the killing effect of PBMC on tumor cell IM9.

Figure 10D:
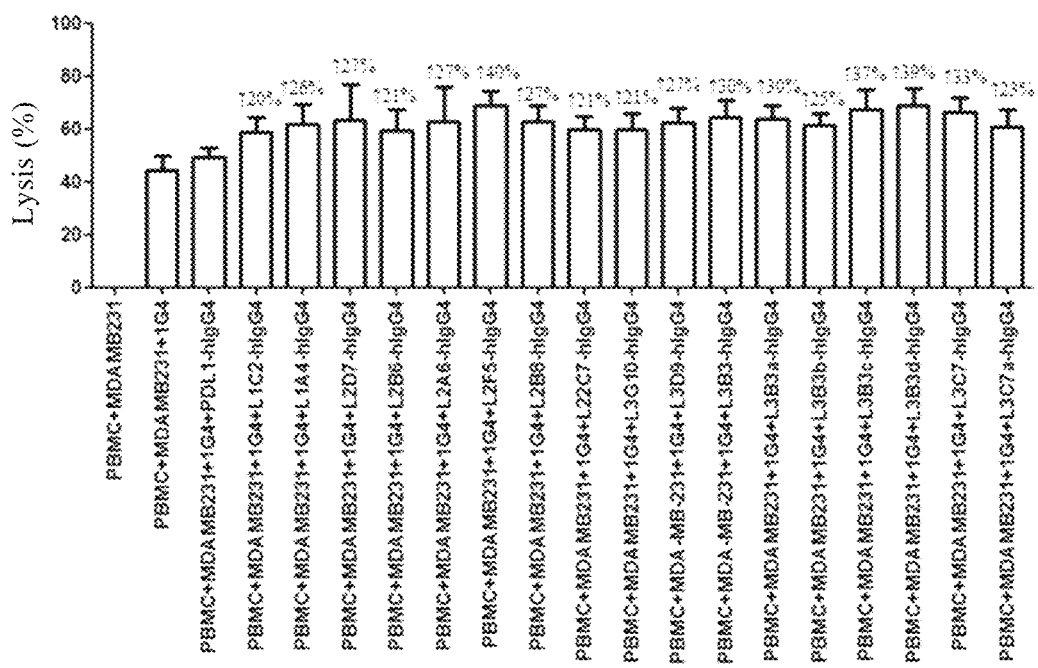
FIG. 10D shows the high-affinity PDL1-hIgG4Fc fusion protein of the present invention significantly increases ImmTAC (1G4)-mediated killing of tumor cell MDA-MB-231 by PBMC.

PDL1-h1gG4 in the histogram of "PBMC+MDA-MB-231+1G4+PDL1-h1gG4" in FIG. 10D was the wild-type PDL-1 fusion molecule. The increase or decrease in the lysis rate in the figure was relative to the "PBMC+MDA-MB-231+1G4+PDL1-h1gG" histogram. The specific calculation was |("PBMC+MDA-MB-231+1G4+High affinity PDL1-h1gG4 molecule"−"PBMC+MDA-MB-231+1G4+PDL1-h1gG4 molecule")|/"PBMC+MDA-MB-231+1G4+PDL1-h1gG4 molecule". This result showed that part of the high-affinity PDL-1 fusion molecule of the present invention significantly enhanced the killing effect of PBMC on tumor cell MDA-MB-231.

The experimental results were shown in FIGS. 10A, 10B, 10C and 10D. The results show that the high affinity PDL1-hIgG4Fc fusion protein of the present invention can significantly increase ImmTAC (1G4)-mediated killing of tumor cells by PBMC.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What we claim:

1. A Programmed Death Ligand-1 (PDL-1) molecule comprising an amino acid sequence selected from the group consisting of SEQ ID NOs: 5-34, wherein the affinity of the PDL-1 molecule to a PD-1 molecule is at least two-fold of the affinity of SEQ ID NO: 1 to the PD-1 molecule.

2. A fusion protein comprising the PDL-1 molecule of claim 1 and hIgG4Fc.

3. A multivalent PDL-1 complex, which comprises at least two PDL-1 molecules, wherein:
   (1) at least one of the at least two PDL-1 molecules of the multivalent PDL-1 complex is the PDL-1 molecule of claim 1; or
   (2) the multivalent PDL-1 complex comprises the fusion protein of claim 2.

4. The multivalent PDL-1 complex of claim 3, which is a bivalent PDL-1 complex, a trivalent PDL-1 complex, or a tetravalent PDL-1 complex.

5. A nucleic acid molecule which comprises a nucleic acid sequence or a complementary sequence thereof encoding the PDL-1 molecule of claim 1 the fusion protein of claim 2, or the multivalent PDL-1 complex of claim 3.

6. A pharmaceutical composition, which comprises a pharmaceutically acceptable carrier and:
   the PDL-1 molecule of claim 1, (2) the fusion protein of claim 2, or
   (3) the multivalent PDL-1 complex of claim 3.

7. The pharmaceutical composition of claim 6, which further comprises immune mobilizing monoclonal T-cell receptors against cancer (ImmTAC) and/or high-affinity T-cell activation core (HATac).

8. A method of treating a tumor expressing a PD-1 molecule in a subject in need thereof, which comprises: administering to the subject a suitable amount of the PDL-1 molecule of claim 1, the fusion protein of claim 2, or the multivalent PDL-1 complex of claim 3.

\* \* \* \* \*